United States Patent [19]

Schally et al.

[11] Patent Number: 5,369,094
[45] Date of Patent: Nov. 29, 1994

[54] POLYPEPTIDE BOMBESIN ANTAGONISTS

[75] Inventors: Andrew V. Schally; Renzhi Cai, both of Metairie, La.

[73] Assignee: The Administrators of the Tulane Educational Fund, New Orleans, La.

[21] Appl. No.: 31,325

[22] Filed: Mar. 15, 1993

Related U.S. Application Data

[63] Continuation-in-part of Ser. No. 619,747, Nov. 29, 1990, Pat. No. 5,244,883.

[51] Int. Cl.$^5$ ............... A61K 37/00; A61K 37/02; C07K 5/00; C07K 7/00
[52] U.S. Cl. ........................ 514/15; 514/14; 514/16; 530/300; 530/328; 530/327
[58] Field of Search ............ 530/323, 324, 325, 326, 530/327, 328, 329, 332, 309, 300; 514/14, 15, 16, 12

[56] References Cited

U.S. PATENT DOCUMENTS

| | | | |
|---|---|---|---|
| 5,068,222 | 11/1991 | Camble et al. | 514/15 |
| 5,081,107 | 1/1992 | Cotton et al. | 514/16 |
| 5,084,555 | 1/1992 | Coy et al. | 530/328 |
| 5,100,873 | 3/1992 | de Castiglione et al. | 514/15 |
| 5,162,497 | 11/1992 | Coy et al. | 530/314 |
| 5,217,955 | 6/1993 | Bogden et al. | 514/12 |

FOREIGN PATENT DOCUMENTS

| | | | |
|---|---|---|---|
| 9102746 | 3/1991 | European Pat. Off. | |
| 9003980 | 4/1990 | WIPO | C07K 4/02 |

OTHER PUBLICATIONS

"Pseudononapeptide Bombesin Antagonists Containing C-Termina Trp or Tpi" Cai, et al. pp. 267–271, Peptides vol. 13, 1992.

"Inhibition of Growth of UT-29 Human Colon Cancer Xenografts in Nude Mice by Treatment with Bombesin/Gastrin Releasing Peptide Antagonist (RC-3095)[1]", Cancer Research 51, 6006–6009, 1991.

Cai et al., Peptides, vol. 13, pp. 267–271, 1992.

Primary Examiner—Lester L. Lee
Assistant Examiner—A. M. Davenport
Attorney, Agent, or Firm—Omri M. Behr; Matthew J. McDonald

[57] ABSTRACT

Pseudopeptides comprising a peptide of formula I:

$$X\text{-}A^1\text{-}A^2\text{-}Trp\text{-}Ala\text{-}Val\text{-}Gly\text{-}His\text{-}Leu_{\text{-}psi\text{-}}A^9\text{-}Q$$

wherein X is hydrogen, a single bond linking the alpha amino group of $A^1$ to the gamma carboxyl moiety on the 3-priopionyl moiety of $A^2$ when $A^2$ is Glu, or a group of formula $R^1CO$— wherein $R^1$ is selected from the groups consisting of a) hydrogen, $C_{1\text{-}10}$alkyl, phenyl or phenyl-$C_{1\text{-}10}$-alkyl, p-HI-phenyl, p-HI-phenyl-$C_{1\text{-}10}$-alkyl, naphthyl, naphthyl-$C_{1\text{-}10}$-alkyl, indolyl, indolyl-$C_{1\text{-}10}$-alkyl, pyridyl, pyridyl-$C_{1\text{-}10}$-alkyl, thienyl, thienyl-$C_{1\text{-}10}$-alkyl, cyclohexyl or cyclohexyl-$C_{1\text{-}10}$-alkyl, where HI=F, Cl, Br, OH, $CH_3$ or $OCH_3$;

b) $N(R^2)(R^3)$—, wherein $R^2$ is hydrogen, $C_{1\text{-}10}$alkyl, phenyl or phenyl-$C_{1\text{-}10}$-alkyl, $R^3$ is hydrogen or $C_{1\text{-}10}$alkyl; c) $R^4O$—, wherein $R^4$ is $C_{1\text{-}10}$alkyl, phenyl or phenyl-$_{1\text{-}10}$-alkyl; $A^1$ is a D- or L- amino acid residue selected from the group consisting of Phe, p-HI-Phe, pGlu, Nal, Pal, Tpi, unsubstituted Trp or Trp substituted in the benzene ring by one or more members selected from the group consisting of F, Cl, Br, $NH_2$ or $C_{1\text{-}3}$alkyl; or $A^1$ is a peptide bond linking the acyl moiety of $R^1CO$— to the alpha amino moiety of $A^2$; $A^2$ is Gln, Glu[—], Glu(Y) or His, wherein [—] is a single bond linking the gamma carboxyl group of $A^2$ when $A^2$ is Glu with the alpha amino group of $A^1$ where X is a single bond, Y is —$OR^5$ or —$N(R^5)(R^6)$ wherein $R^5$ is hydrogen, $C_{1\text{-}3}$alkyl or phenyl; $R^6$ is hydrogen or $C_{1\text{-}3}$alkyl; and $R^7$ is hydrogen, $C_{1\text{-}3}$alkyl or —$NHCONH_2$; Leu-$y_{psi}$- is a reduced form of Leu wherein the C=O moiety of Leu is instead —$CH_2$— such that the bond of this —$CH_2$— moiety with the alpha amino moiety of the adjacent $A^9$ residue is a pseudopeptide bond; $A^9$ is Tac, MTac, or DMTac; and Q is $NH_2$ or $OQ^1$ where $Q^1$ is hydrogen, $C_{1\text{-}10}$alkyl, phenyl or phenyl-$C_{1\text{-}10}$-alkyl; and the pharmaceutically acceptable acids or salts thereof.

20 Claims, 3 Drawing Sheets

POLYPEPTIDE BOMBESIN ANTAGONISTS

This invention was made with Government support under grant No. CA 40077, awarded by the N.C.I. (NIH). The U.S. Government has certain rights in this application.

RELATED APPLICATIONS

This application is a continuation-in-part of application Ser. No. 07/619,747, filed Nov. 29, 1990 by Schally and Cai, (now issued at U.S. Pat. No. 5,244,883) who are the Assignors of said application to The Administrators of The Tulane Educational Fund. Both Schally and Cai were obliged to assign the present invention ab initio.

FIELD OF THE INVENTION

The present invention is directed to novel peptides which influence the growth of cancerous tumors in humans. More specifically, the present invention relates to bombesin antagonists which are $\Psi^{8-9}$ pseudopeptides containing a Tac, MTac, or DMTac residue at the C terminal position, the salts thereof, and pharmaceutical compositions, methods of synthesizing these peptides and methods of use pertaining to these peptides. These peptides possess antagonist properties against bombesin or bombesin-like peptides.

BACKGROUND OF THE INVENTION

This invention relates to polypeptide compounds which possess antagonist properties against bombesin or bombesin-like peptides (such as gastrin releasing peptide (GRP), Neuromedin C and the like) hereinafter referred to as bombesin antagonist properties and which are of value, for example in the treatment of malignant diseases in warm-blooded organisms such as man. The invention includes novel polypeptide compounds and processes for their manufacture; novel pharmaceutical compositions containing said polypeptide compounds and processes for the manufacture of medicaments containing them for use in producing a bombesin antagonist effect in warm-blooded organisms such as man.

Bombesin is a tetradecapeptide amide which was first isolated from the skin of the frog *Bombina bombina* (Anastasi, Erspamer and Bucci, *Experientia*, 1971, 27, 166). It is known that bombesin is a potent mitogen for mouse Swiss 3T3 fibroblast cells (Rozengurt and Sinnett-Smith, *Proc. Natl. Acad. Sci. USA*, 1983, 80, 2936) and that it stimulates amylase secretion from guinea pig pancreatic acini (Jensen, Jones, Folkers and Gardner, *Nature*, 1984, 309, 61). It is also known that bombesin-like peptides are produced and secreted by human small-cell lung cancer (SCLC) cells (Moody, Pert, Gazdar, Carney and Minna, *Science*, 1981, 214, 1246), that exogenously added bombesin-like peptides can stimulate the growth of human SCLC cells in vitro (Carney, Cuttita, Moody and Minna, *Cancer Research*, 1987, 47, 821) and that a monoclonal antibody specific for the C-Terminus region of bombesin and GRP can block binding of GRP to its receptors and prevent the growth of human SCLC cells both in vitro and in vivo (Cuttita, Carney, Mulshine, Moody, Fedorko, Fischler and Minna, *Nature*, 1985, 316, 823).

GRP which has bombesin-like properties is a widely distributed peptide amide containing 27 amino acids isolated from the porcine gut (McDonald, Jornvall, Nilsson, Vagne, Ghatei, Bloom and Mutt, *Biochem. Biophys. Res. Commun.*, 1979, 90, 227) in which the C-terminus amino acid sequence is almost identical to that of bombesin. Neuromedin C is a decapeptide amide, the structure of which is identical to the last ten amino acids in the C-terminus region of GRP, which has been isolated from the canine small intestine (Reeve, Walsh, Chew, Clark, Hawke and Shively, *J. Biol. Chem.*, 1983, 258, 5582). GRP stimulates a variety of biological responses, including the release of gastrin in the systemic circulation. It also functions as a growth factor in 3T3 mouse fibroblasts and small cell lung cancer (SCLC) cell. So GRP has been proposed to play a direct pathophysiological role in the development of SCLC via an autocrine growth mechanism.

The structures of bombesin, Neuromedin C and Carboxyl-terminal nonapeptide of GRP are shown below:

| | | |
|---|---|---|
| Bombesin | pGlu—Gln—Arg—Leu—Gly—Asn—Gln—Trp—Ala—Val—Gly—His—Leu—Met—NH$_2$ | Seq ID No. 23 |
| Neuromedin C | H—Gly—Asn—His—Trp—Ala—Val—Gly—His—Leu—Met—NH$_2$ | Seq ID No. 24 |
| C-terminal nonapeptide of GRP | Asn—His—Trp—Ala—Val—Gly—His—Leu—Met—NH$_2$ | Seq ID No. 25 |

The search for other amphibian bombesin-like peptides led to the isolation of Litorin, a nonapeptide (pGlu-Gln-Trp-Ala-Val-Gly-His-Leu-Met-NH$_2$) in the skin of frog from Papua, New Guinea which proves to be an extremely potent bombesin analogues (Yasukara et al., *Chem. Pharm. Bull.*, 1979, 27, 492). The studies on bombesin analogues revealed that a minimum segment of the 9 amino acid residues from position 6 to 14 of bombesin possessed the full spectrum of bombesin activity.

Several kinds of bombesin antagonists have now been characterized. Substance P (Arg-Pro-Lys-Pro-Gln-Gln-Phe-Phe-Gly-Leu-Met-NH$_2$) Seq. ID No. 26 which has slight amino acid sequence homology with bombesin does not inhibit the binding of bombesin and bombesin-like peptides, but Substance P analogues modified by the replacement of several of L-amino acids with D-amino acids such as (D-Arg$^1$, D-Pro$^2$, D-Trp$^{7,9}$, Leu$^{11}$) Substance P and (D-Arg$^1$, D-Phe$^5$, D-Trp$^{7,9}$, Leu$^{11}$) Substance P, (Moody et al., Fed. Proceedings, 1987, 46, 2201) were found to block the secreting of bombesin in pancreatic acinar cells and to antagonize the growth-promoting effects of bombesin in Swiss 3T3 cells. Two types of bombesin antagonists derived from bombesin, for instance, (D-Phe$^6$, D-Phe$^{12}$) bombesin, and [Leu$^{13}$-$_{psi}$-Leu$^{14}$] bombesin (Coy et al., *J. Biol. Chem.*, 1988, 263, 5056 and peptides, 1989, 10, 587) have proved to be potent in vitro and in vivo inhibitors of bombesin response.

Another type of bombesin antagonist revealed by Heimbrook et al., (Bio. Chem., 1989, 264, 11258) is N-acetyl-GRP(20-26) and its analogues, wherein the C-terminal methionine residue is deleted from GRP(20-27) analogues. Coy [*J. Biol. Chem.*. 264, 1989, 25, 14691] reported that some short chain bombesin antagonists based on Litorin sequence such as [D-Phe$^b$ 6, Leu$^{13}$-$_{psi}$-Phe$^{14}$] bombesin-(6-14) and [D-Phe$^6$, Leu$^{13}$-$_{psi}$-Leu$^{14}$] bombesin-(6-14) exhibited much more potency than their corresponding parent peptide [Leu$^{13}$-$_{psi}$-Leu$^{14}$] bombesin.

Linear (non-cyclic) bombesin analogues of GRP and amphibian bombesin optionally having a CH$_2$—NH non-peptide bond are described in PCT Patent Application WO 90/03980 (and related analogues in WO 91/02746). These analogues, said to act as inhibitors of natural bombesin peptides, have the formula

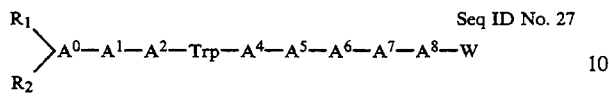

Seq ID No. 27 where R$_1$ and R$_2$=H; A° may be deleted; among the many possible amino acids at each position, A$^1$ may=D-Phe, D-Trp, or D-Nal; A$^2$ may=Gln; A$^4$ may=Ala; A$^5$ may=Val; A$^6$ may=Gly; A$^7$ may=His; and W=

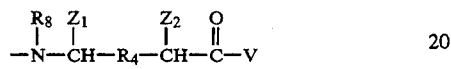

where R$_4$=CH$_2$—NH; in some circumstances, Z$_1$ may = the identifying side chain of Leu, i.e., —CH$_2$CH(CH$_3$)$_2$; Z$_2$ may = the identifying side chain of Cys or Met, i.e., —CH$_2$—SH or (CH$_2$)$_2$—S—CH$_3$; V=N(R$_6$)R$_7$, where R$_6$, R$_7$, and R$_8$ may=H; R$_1$ and R$_2$ may=H or COE$_1$, where E$_1$ may=C$_{1-20}$ alkyl.

Linear peptide analogs of bombesin are also described in EP 0 309 297. These peptides may have C-terminal Met residue and a [CH$_2$—NH] pseudopeptide bond between the C-terminal and its adjacent residue.

SUMMARY OF THE INVENTION

The present invention provides novel polypeptides which are potent bombesin antagonists; methods of synthesizing these polypeptides; and medical applications including pharmaceutical compositions comprising said polypeptides and of said polypeptides and compositions as pharmaceutically active agents.

A. Synthetic Peptides

More particularly, a first embodiment provides potent bombesin antagonist pseudopeptides of Formula I:

Seq ID No. 28
X—A$^1$—A$^2$—Trp—Ala—Val—Gly—His—Leu-psi-A$^9$—Q   I wherein
X is hydrogen,
  a single bond linking the alpha amino group of A$^1$ to the gamma carboxyl moiety on the 3-propionyl moiety of A$^2$ when A$^2$ is Glu, or
  a group of formula R$^1$CO—, wherein R$^1$ is selected from the groups consisting of
    a) hydrogen, C$_{1-10}$ alkyl, phenyl, phenyl-C$_{1-10}$-alkyl, p-HI-phenyl, p-HI-phenyl-C$_{1-10}$-alkyl, naphthyl, naphthyl-C$_{1-10}$-alkyl, indolyl, indolyl-C$_{1-10}$-alkyl, pyridyl, pyridyl-C$_{1-10}$-alkyl, thienyl, thienyl-C$_{1-10}$-alkyl, cyclohexyl or cyclohexyl-C$_{1-10}$-alkyl, e.g. where HI=F, Cl, Br, OH, CH$_3$ or OCH$_3$;

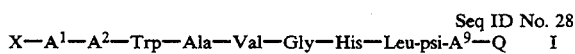

wherein
  R$^2$ is hydrogen, C$_{1-10}$ alkyl, phenyl or phenyl-C$_{1-10}$-alkyl,
  R$^3$ is hydrogen or C$_{1-10}$ alkyl;
  c) R$^4$—O wherein R$^4$ is C$_{1-10}$ alkyl, phenyl or phenyl-C$_{1-10}$-alkyl;

A$^1$ is a D-, L- or DL-amino acid residue selected from the group consisting of Phe, p-HI-Phe, pGlu, Nal, Pal, Tpi, unsubstituted Trp or Trp substituted in the benzene ring by one or more members selected from the group consisting of F, Cl, Br, NH$_2$ or C$_{1-3}$ alkyl; or a peptide bond linking the acyl moiety of R$^1$CO— to the alpha amino moiety of A$^2$;

A$^2$ is Gln, Glu [—], Glu (Y), or His, wherein
  [—] is a single bond, when X is a single bond and A$^2$ is Glu, linking the gamma carboxyl moiety or the 3-propionyl moiety A$^2$ with the alpha amino moiety of A$^1$, Y is
  a) —OR$^5$ wherein R$^5$ is hydrogen, C$_{1-3}$ alkyl or phenyl; or
  b)

wherein R$^6$ is hydrogen or C$_{1-3}$ alkyl;
  R$^7$ is hydrogen, C$_{1-3}$ alkyl or —NHCONH$_2$, and Leu-$psi$- is a reduced form of Leu wherein the C=O moiety of Leu is instead —CH$_2$— such that the bond of this —CH$_2$— moiety with the alpha amino moiety of the adjacent A$^9$ residue is a pseudopeptide bond;

A$^9$ is Tac, MTac, or DMTac; and

Q is NH$_2$ or —OQ$^1$ where Q$^1$ is hydrogen, C$_{1-10}$ alkyl, phenyl or phenyl-C$_{1-10}$-alkyl; and the pharmaceutically acceptable acids or salts thereof.

When A$^1$ is a single bond, the pseudopeptide of Formula I is an octapeptide, but when A$^1$ is an amino acid, or an analog thereof, the pseudopeptide is a nonapeptide.

Where A$^9$=Tac, MTac or DMTac, there is present at A$^9$ a 5-membered heterocyclic ring. This ring is generally formed by oxidizing the A$^9$ residue's side chain at some point in the synthesis of the Formula I nonapeptide, preferably with formaldehyde or acetaldehyde to cyclize the sidechain with the alpha amino group of A$^9$. The identity of the resulting cyclized A$^9$ residue depends on the identity of the original, unoxidized A$^9$ and the oxidizing reagent used thereon.

Thus, when the —CH$_2$—SH group of Cys$^9$ cyclizes with the Cys$^9$ alpha amino group adjacent the Leu-$psi$-pseudopeptide linkage in a reaction with formaldehyde, the resulting ring has the structure of Formula IIA (shown here as the -Leu$^8$-$psi$-TAC$^9$-NH$_2$ fragment of the Formula I nonapeptide):

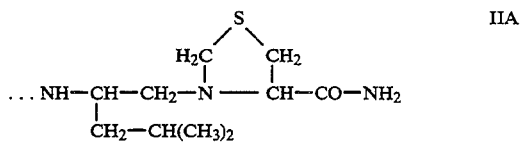

These pseudopeptides have greater biological activity and longer stability than those non-ring embodiments where $A^9$ is Cys or Pen. Nevertheless, in certain preferred embodiments of the Formula I peptides where $A^9$ is non-cyclized, X, $A^2$, and Q are as above, $A^9$ is Cys or Pen, and $A^1$ is a non-naturally occurring amino acid selected from the group consisting of L- or D-Pal, L- or D-Tpi or Hca.

In certain preferred embodiments, X is $R^1CO$, $R^1$ is hydrogen or $C_{1-10}$ alkyl (preferably methyl); $A^1$=D-Cpa, D-Nal, D-Phe, D- or L-Tpi, or D-Trp; $A^2$=Gln; $A^9$=Tac or DMTac; and Q=NH$_2$.

When however, in other preferred embodiments, $A^1$ is a peptide bond linking the acyl moiety of $R^1CO-$ to the alpha amino group of $A^2$, then $A^2$ is Gln or His;

$A^9$ is Tac, M-Tac or DM-Tac, and Q is NH$_2$. In a preferred from of these peptides, X is Hca, Hna, Paa, Mpp, Hpp or Naa; $A^2$ is Gin and $A^9$ is Tac.

B. Synthetic Methods

The bombesin antagonists of Formula I may be synthesized by solid phase synthesis. In a first protocol, all the amino acids are sequentially linked to one another after the C-terminal residue has been linked to the resin support phase. Once all the amino acyl residues are linked to the resin, the pseudopeptide's 5-membered heterocyclic ring is formed by reaction of the side chain of the C-terminal residue with an oxidizing reagent. The pseudopeptide is then subjected to HF treatment to remove it from the resin support phase. This reaction also removes the side chain protecting groups.

In a second protocol, the pseudopeptides of Formula I may be synthesized as two fragments which are built by solid phase or liquid phase. A tripeptide containing C-terminal is linked with an oligopeptide to form the entire Formula I bombesin antagonist.

The 5 member heterocyclic ring is formed by reaction of the $A^9$ side chain with an oxidizing reagent. The peptide is then subjected to HF treatment, which removes all the amino acyl residue side chain protecting groups and cleaves the peptide from the resin.

C. Medical Applications

The pseudopeptides of Formula I may be employed in pharmaceutical compositions to treat certain mammalian cancers as well as other conditions, by administering an effective dose of the pseudopeptide, or a therapeutically acceptable acid or salt thereof in a pharmaceutical carrier. They may be administered with a pharmaceutically acceptable carrier at dosages of from about 1 to 1,000 micrograms per kg of body weight daily. Such a composition may be administered parenterally, intravenously, subcutaneously, intramuscularly, intranasally, by pulmonary aerosol or in depot form.

DESCRIPTION OF THE PREFERRED EMBODIMENTS

A. Synthetic Peptides

1. Nomenclature

Figure 1:
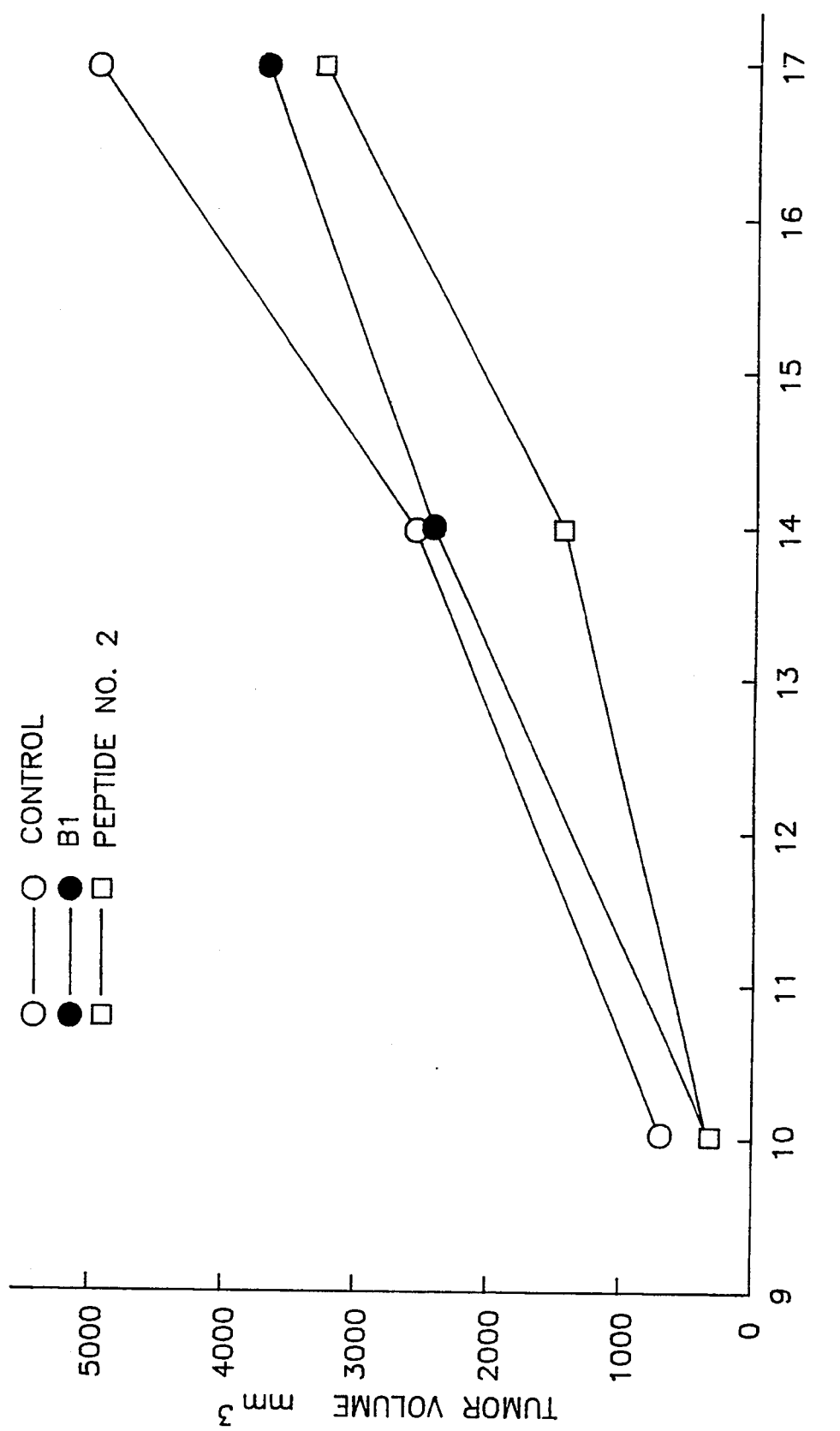
FIG. 1 is a graph depicting the effect of an MXT mouse mammary cancer of administering certain bombesin antagonists, based on data drawn from Table 2, Example 7.

For convenience of describing this invention, the conventional abbreviations for amino acids, peptides and their derivatives are used as generally accepted in the peptide art and as recommended by the IUPAC-IUB Commission on Biochemical Nomenclature [*European J. Biochem.*, 1984, 138 9-37].

The abbreviations for the individual amino acid residues are based on the trivial name of the amino acid, e.g. Ala is alanine, Cys is cysteine, Gln is glutamine, Glu is glutamic acid, pGlu is pyroglutamic acid, Gly is glycine, His is histidine, Leu is leucine, Phe is phenylalanine, Trp is tryptophan, and Val valine. Glu may have functional groups linked to its gamma carboxyl side chain: [—] or Y, defined above. Dpa is 2,3-diaminopropionic acid. Where the amino acid residue has isomeric forms, it is the L-form of the amino acid that is represented unless otherwise indicated by D- or DL- appearing before the amino acid symbol.

Abbreviations of the uncommon amino acids employed in the present invention are as follows:

Cpa is para-chlorophenylalanine
Dpa is 2,3-diaminopropionic acid
pGlu is pyroglutamic acid
Nal is 3-(2-naphthyl)-alanine
Pal is 3-(3-pyridyl)-alanine
Pen is penicillamine
Tpi is 2,3,4,9 tetrahydro-1 H-pyrido-[3,4-b] indole-3-carboxylic acid
Tac is thiazolidine-4-carboxylic acid
MTac is 2-Methyl-thiazolidine-4-carboxylic acid
DMTac is 5,5-Dimethyl-thiazolidine-4-carboxylic acid Amino acid analogues include:

Hca is hydrocinnamic acid or des-amino-phenylalanine
Hna is 3-hydroxy-2-naphthoic acid
Hpp is 3-(4-hydroxyphenyl)propionic acid
Mpp is 3-(4-methoxyphenyl)propionic acid
Naa is naphthyl acetic acid
Paa is phenylacetic acid Other abbreviations used are:

AC acyl
Ac acetyl
AcOH acetic acid
BHA benzhydrylamine
Boc tert-butoxycarbonyl
(BOC)$_2$-di-tert-butyldicarbonate
Bom benzyloxymethyl
But butyl
Bzl benzyl
BSA bovine serum albumin
DIC 1,3-diisopropylcarbodiimide
DMEM Dulbecco's modified Eagle's medium
DMF dimethylformamide
Et ethyl
EDTA ethylene diamine tetraacetic acid
FCBS fetal calf bovine serum
Fmoc 9-fluorenylmethyloxycarbonyl
For formyl
HITES RPMI 16 4D medium plus $10^{-8}$M hydrocortisone, 5 ul/ml bovine insulin, 10 ug/ml human transferrin, $10^{-8}$M β-estradiol and $3 \times 10^{-8}$ M $Na_2SeO_3$
HOBt 1-hydroxybenzotriazole
HPLC high-performance-liquid-chromatography
Leu-$psi$-is a reduced form of Leu where the C=O bond moiety of Leu is instead —$CH_2$— such that the bond of this —$CH_2$— moiety with the amino moiety of $A^9$ is a pseudopeptide bond
Me methyl
MeCN acetonitrile
MeOH methyl alcohol
PBS phosphate-buffered saline
TEA triethylamine
TFA trifluoroacetic acid Peptide sequences are written according to the convention whereby the N-terminal amino acid is on the left and the C-terminal amino acid is on the right. It should be noted however that the convention of numbering amino acid residues in a fragmentary peptide according the corresponding position in the complete bombesin antagonist tetradecapeptide is not followed herein unless otherwise noted. If this convention were followed, the residues in the Formula I nonapeptide described herein would be numbered from 6 through 14, and the Trp-Ala-Val-Gly-His-Leu core of the bombesin antagonists would be numbered $A^8$-$A^9$-$A^{10}$-$A^{11}$-$A^{12}$-$A^{13}$. To avoid confusion, the bombesin antagonists are instead numbered herein as follows: the N-terminal amino acid (or amino acid analogue) residue is $A^1$; the C-terminal amino acid residue (or amino acid analogue) is $A^9$; and the intervening residues are numbered sequentially from $A^2$ (adjacent the N-terminal residue $A^1$) in increasing numbers to $A^8$ (adjacent the C-terminal residue $A^9$).

Preferred Embodiments

The preferred embodiments are bombesin antagonist peptides of Formula I $$X—A^1—A^2—Trp—Ala—Val—Gly—His—Leu\text{-psi-}A^9—Q \quad \text{I}$$
Seq ID No. 28 wherein X, $A^1$, $A^2$, Leu-$psi$, $A^9$ and Q are defined as above.

These bombesin antagonist pseudopeptides are characterized by amino acid sequence, particularly at residues $A^1$, $A^2$ and $A^9$; as well by the presence of a pseudopeptide bond between $A^8$ and $A^9$; and optionally by a 5-membered heterocyclic ring at $A^9$. The ring structure is determined by the identity of the $A^9$ residue and the compound used to oxidize it. Thus, when formaldehyde is employed and $A^9$ is Cys, the resulting ring has the structure Tac of Formula IIA shown here as the Leu$^8$-$psi$-Tac$^9$-Q fragment of the Formula I peptide where Q=$NH_2$):

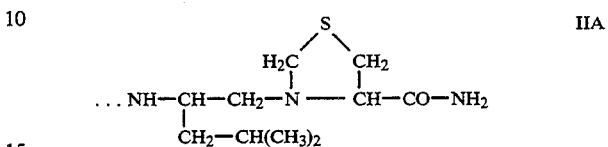

When Cys is instead oxidized with acetaldehyde, the resulting 5-membered heterocyclic ring has the structure MTac of formula IIB (shown here as the Leu$^8$-$psi$-MTac$^9$-Q fragment of the Formula I peptide where Q=$NH_2$):

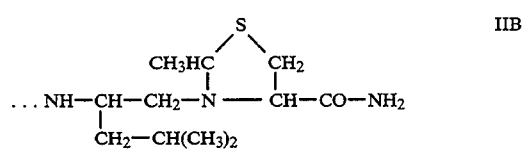

When $A^9$ is instead Pen and is oxidized by formaldehyde, the resulting ring has the structure DMTac of Formula IIC (shown here as the -Leu$^8$-$psi$-DMTac$^9$-Q fragment of the Formula I nonapeptide where Q=$NH_2$):

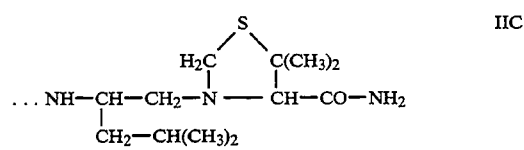

In these preferred embodiments it is desirable that X=H or Ac, $A^1$=D-Phe, $A^2$=Gln and Q=$NH_2$.

The most particularly preferred pseudopeptide bombesin antagonists in the present invention appear below.

| Peptide No. | Structure | |
|---|---|---|
| 1. | D—pGlu—Gln—Trp—Ala—Val—Gly—His—Leu-psi-Tac—$NH_2$ | Seq ID No. 1 |
| 2. | D—Phe—Gln—Trp—Ala—Val—Gly—His—Leu-psi-Tac—$NH_2$ | Seq ID No. 2 |
| 3. | D—Phe—Gln—Trp—Ala—Val—Gly—His—Leu-psi-MTac—$NH_2$ | Seq ID No. 3 |
| 4. | Ac—D—Phe—Gln—Trp—Ala—Val—Gly—His—Leu-psi-Tac—$NH_2$ | Seq ID No. 4 |
| 5. | D—Cpa—Gln—Trp—Ala—Val—Gly—His—Leu-psi-Tac—$NH_2$ | Seq ID No. 5 |
| 6. | D—Cpa—Gln—Trp—Ala—Val—Gly—His—Leu-psi-MTac—$NH_2$ | Seq ID No. 6 |
| 7. | D—Nal—Gln—Trp—Ala—Val—Gly—His—Leu-psi-Tac—$NH_2$ | Seq ID No. 7 |
| 8. | Pal—Gln—Trp—Ala—Val—Gly—His—Leu-psi-Tac—$NH_2$ | Seq ID No. 8 |
| 9. | D—Pal—Gln—Trp—Ala—Val—Gly—His—Leu-psi-Tac—$NH_2$ | Seq ID No. 9 |
| 10. | D—Trp—Gln—Trp—Ala—Val—Gly—His—Leu-psi-Tac—$NH_2$ | Seq ID No. 10 |
| 11. | Ac—D—Trp—Gln—Trp—Ala—Val—Gly—His—Leu-psi-Tac—$NH_2$ | Seq ID No. 11 |
| 12. | Tpi—Gln—Trp—Ala—Val—Gly—His—Leu-psi-Tac—$NH_2$ | Seq ID No. 12 |

-continued

| Peptide No. | Structure | |
|---|---|---|
| 13. | D—Tpi—Gln—Trp—Ala—Val—Gly—His—Leu-psi-Tac—NH$_2$ | Seq ID No. 13 |
| 14. | Hca—Gln—Trp—Ala—Val—Gly—His—Leu-psi-Tac—NH$_2$ | Seq ID No. 14 |
| 15. | D—Phe—His—Trp—Ala—Val—Gly—His—Leu-psi-Tac—NH$_2$ | Seq ID No. 15 |
| 16. | D—Phe—Glu(OMe)—Trp—Ala—Val—Gly—His—Leu-psi-Tac—NH$_2$ | Seq ID No. 16 |
| 17. | ⌐D—Phe—Glu[-]—Trp—Ala—Val—Gly—His—Leu-psi-Tac—NH$_2$ | Seq ID No. 17 |
| 18. | D—Phe—Gln—Trp—Ala—Val—Gly—His—Leu-psi-DMTac—NH$_2$ | Seq ID No. 18 |
| 19. | Ac—D—Phe—Gln—Trp—Ala—Val—Gly—His—Leu-psi-DMTac—NH$_2$ | Seq ID No. 19 |
| 20. | D—Cpa—Gln—Trp—Ala—Val—Gly—His—Leu-psi-DMTac—NH$_2$ | Seq ID No. 20 |
| 21. | Tpi—Gln—Trp—Ala—Val—Gly—His—Leu-psi-DMTac—NH$_2$ | Seq ID No. 21 |
| 22. | D—Tpi—Gln—Trp—Ala—Val—Gly—His—Leu-psi-DMTac—NH$_2$ | Seq ID No. 22 |

Especially preferred embodiments include the following:

| 2. | D—Phe—Gln—Trp—Ala—Val—Gly—His—Leu-psi-Tac—NH$_2$ | Seq ID. No. 2 |
|---|---|---|
| 13. | D—Tpi—Gln—Trp—Ala—Val—Gly—His—Leu-psi-Tac—NH$_2$ | Seq ID No. 13 |
| 18. | D—Phe—Gln—Trp—Ala—Val—Gly—His—Leu-psi-DMTac—NH$_2$ | Seq ID No. 18 |

B. SYNTHETIC METHODS

1. Overview

The pseudopeptides of Formula I may be prepared by any techniques that are known to those skilled in the peptide art. A summary of the techniques so available can be found in M. Bodanszky, Principles of Peptide Synthesis, Springer-Verlag, Heidelberg, 1984.

All the Formula I pseudopeptides may be synthesized according to the procedures of solid phase synthesis. A particularly preferred method of preparing these peptides and their intermediate peptides is solid phase synthesis. The techniques of exclusively solid-phase synthesis are set forth in the textbook of J. M. Stewart and J. D. Young, Solid Phase Peptide Synthesis, Pierce Chem. Co., Rockford, Ill., 1984 (2nd. ed.) and in the review of G. Barany, et al., Int. J. Peptide Protein Res., 30, 705-739, 1987. (The additional step of oxidizing the C-terminal A$^9$ residue to cyclize the residue's characteristic side chain with its alpha amino group may be performed at one of several points of synthesis of the Formula 1 peptides.

At least two synthetic protocols may be followed to produce the Formula I pseudopeptide bombesin antagonists. In the first protocol, all the amino acids are sequentially linked to one another after the C-terminal residue, A$^9$ has been linked to a resin support phase. In the second protocol, a tripeptide is built on the resin. It is then linked to an oligopeptide carrying the remainder of the amino acid to form the bombesin antagonist. In both protocols, synthesis begins at the C-terminal A$^9$ residue and adds amino acid residues sequentially with growth toward the N-terminal residue.

1. (a) First Protocol. The resin support phase employed in the solid phase synthesis of the pseudopeptides may be benzhydrylamine (BHA) resin or chloromethylated polystyrene resin 1% crosslinked with divinylbenzene, which are both commercially available. The C-terminal A$^9$ residue is attached to this resin via its carboxyl group. Reaction between two of these residues is prevented by attaching a chemical protecting group at the alpha amino group of each A$^9$ residue prior to linking it to the resin. The protecting group for the alpha amino group of the A$^9$ residue, and each subsequently linked amino acid residue, may be either 9-fluorenylmethyloxycarbonyl (Fmoc) or tert-butoxycarbonyl (Boc) group. Fmoc is preferred in coupling the C-terminal residue A$^9$ through A$^2$ since the reaction removing Boc also removes the side chain protecting group from the C-terminal A$^9$ residue. During these linking reactions, the characteristic side chain functional groups of certain amino acid residues may also be protected from undesired chemical reaction by attaching a chemical protecting group thereto (suitably But for A$^9$) prior to the linkage reaction.

After the C-terminal Fmoc-A$^9$(But) residue is joined to the support phase, its alpha amino group is deprotected and Fmoc-Leu-CHO is coupled thereto, thus forming the pseudopeptide bond.

The remaining residues, A$^5$, A$^4$, A$^3$ and A$^2$, suitably protected by Fmoc, and A$^1$ suitably protected by Boc, are added step-wise in reverse numerical order (A 7, A$^6$, etc.) to construct the desired pseudopeptide.

When His or Glu is present in the pseudopeptide, their side chains may be vulnerable to undesirable chemical reactions during their linking reactions or the linking reactions of other residues. Accordingly, a chemical protecting group may be attached to such side chains, prior to linking these amino acids in the linking reaction.

Once all the amino acid residues are linked to the BHA resin, the pseudopeptide's Boc at the N-terminal may be removed. The Tac, MTac or DMTac 5-membered heterocyclic ring is formed by reaction of the exposed —CH$_2$—SH moiety of Cys (or the —C(CH$_3$)$_2$SH of Pen) and the secondary amino of the reduced bond joining residues A$^8$ and A$^9$ (i.e., the alpha amino of A$^9$) with an oxidizing reagent, such as formaldehyde or acetaldehyde. The intermediate pseudopeptide, still bearing side chain protecting groups, is subjected to HF treatment to cleave it from the resin support phase and also to remove the side chain protecting groups.

1(b) Second Protocol.

In the second protocol, following solid phase synthesis pathways, the tripeptide is built up on the BHA resin to the protected tripeptide resin:

Boc-His(Bom)$^7$-Leu$^8$-$_{psi}$-Cys(But)$^9$-BHA resin

The Boc$^1$ group and the But group are removed and the —CH$_2$—SH moiety of Cys is cyclized with the secondary amine of the reduced bond joining residues A$^8$ and A$^9$ to get His (Bom)$^7$-Leu$^8$-psi-Tac$^9$-BHA resin. After HF treatment, the free tripeptide His$^7$-Leu$^8$-psi-Tac$^9$-NH$_2$ is obtained. Boc A$^1$-A$^2$-Trp-Ala-Val-Gly-OCH$_2$-resin is built step by step on Gly-OCH$_2$-resin in accordance with the standard methods of solid phase synthesis, and then treated in 95% methanol containing 1% KCN for 12 hours to cleave the Boc-oligopeptide. After the two fragments are constructed, the Boc-oligopeptide is linked to the free His$^7$-Leu$^8$-$_{psi}$-Tac$^9$-NH$_2$ tripeptide with BOP reagent. The Boc group of is then removed to yield the desired peptide.

Before describing synthesis of the Formula I bombesin antagonists in detail, several synthetic Operations common to one or both of the above protocols are described.

2. General Operations for Polypeptide Synthesis

Operation 1: Formation of certain synthetic residues or reactants a) L- and D-Tpi: 2.04 g (10 mM) of L-Trp is dissolved in 25 ml of boiling water containing 2.1 g of citric acid. 0.5 ml 40% aqueous formaldehyde are added and solids begins to form immediately. The mixture is chilled in an ice bath and the precipitates collected and washed with cold water and air, then dried at room temperature to yield 2.14 g or 99% solids m.p. with (decomposition) ca. 310°. The D-isomer is formed in the same manner from D-Trp and also has m.p. (decomposition) ca. 310° C.

b) L- and D-Boc-Tpi: To a stirred suspension of 10.8 g (50 mM) of D-Tpi in 250 ml of 0.2N NaOH and 7.5 ml triethyl amine was added 10 g of Di-tertbutyl dicarbonate, the mixture stirred 4 hrs then another 10 g of dicarbonate added and a further 10 g after another 3 hrs. of stirring. The mixture is stirred overnight and extracted (2×100 ml) with ether, which is discarded. Citric acid was added to the aqueous layer to reach a pH of 3-5. The solids are collected, washed with water and air dried overnight.

The solids are suspended in 100 ml tetrahydrofuran. Almost all solids dissolved. The insolubles are removed by filtration and THF removed under vacuum. The residue is triturated with ether to yield 9.20 g or 58%. This material has same m.p. as the starting material, but differs in solubility and TLC on silica using 85:15:0.5 CHCl$_3$: MeOH:HOAc.

2.55 g of L-Tpi gives 2.22 g or 59% of Boc-Tpi using the same method.

c) Fmoc-Leu-CHO

Fmoc-Leucine methyl ester (35 g, 134 mmoles) in dry toluene (250 ml) under N$_2$ is cooled with dry ice/acetone, and 150 ml of 25 % di-isobutyl-aluminum hydride in toluene are added over 30 mins. The mixture is stirred for 20 min in a bath of dry ice/acetone after the addition of the di-isobutyl aluminum hydride, then methanol (15 ml) is added cautiously. The mixture is poured into 1000 ml ice-cold water, shaken and filtered. The toluene is separated and the aqueous phase re-extracted with ether (3×300 ml). Toluene and ether extracts are combined and dried over Na$_2$SO$_4$. The resulting oil is passed rapidly though a silica gel column (3×50 cm) in 1500 ml 15% EtOAc/petrol. The Fmoc-Leu-CHO is obtained as a solid (27.6 g).

d) Synthetic amino acids or amino acid analogs to be incorporated in the bombesin antagonist pseudopeptides are generally available from commercial sources. Thus, Hca is commercially available from Aldrich Co., 1001 St. Paul Avenue, Milwaukee, Wis. 53233. Boc- or Fmoc-protected amino acids are available commercially from Advanced ChemTech, 5609 Fern Valley Road, Louisville, Ky. 40228; or Bachem Calif., 3132 Kashiwa Street, Torrance, Calif. 90505.

Operation 2: Preparation of resin and addition of A$^9$ residue,

The BHA resin is prepared by treatment with 10% TEA in CH$_2$Cl$_2$ (neutralization) twice each for three minutes and washed with CH$_2$Cl$_2$ six times. The Fmoc-A$^9$(But) residue is bound to the resin by adding with 1.35 mmole Fmoc-A$^9$(But) and 1.50 mmoles 1-hydroxybenzotriazole (HOBt) in DMF and mixing for three minutes. 20% 1,3-diisopropyl-carbodiimide (DIC) with 1.3 mmoles in CH$_2$Cl$_2$ is added. The mixture is shaken at room temperature for 60 minutes. The resulting Fmoc-A$^9$(But)-BHA resin is washed with CH$_2$Cl$_2$, methanol two times each, and CH$_2$Cl$_2$ three times, and then subjected to a Kaiser test (Anal. Biochem. 34, 595 (1970)). In case of incomplete coupling, the procedure is repeated.

Operation 3: Formation of pseudopeptide bond

The deprotection of Fmoc group from A$^9$ is performed by adding 50% piperidine in DMF and mixing for 30 min; washing with DMF (6×1 min); then i) adding Fmoc-Leu-CHO (3 equiv.) in DMF containing 1% AcOH; and ii) adding NaBH$_3$CN (3.5 equiv.) in DMF and shaking 60 min. This is followed by washing with 50% MeOH (3×1 min); 100% MeOH (3×1 min); and DMF (3×1 min).

Operation 4: Coupling of amino acids and Formation of peptide bond

The protecting group for the alpha amino group of the A$^9$ residue, and each subsequently linked amino acid residue, may be either 9-fluorenylmethyloxy-carbonyl (Fmoc) or tert-butoxycarbonyl (Boc) group. Fmoc is preferred in coupling A$^9$ through the amino acid residue just adjacent the N-terminal amino acid residue since the reaction removing Boc also removes the side chain protecting group of A$^9$.

A) Using Fmoc-amino acid

The following procedures are performed for introducing an Fmoc amino acid to an Fmoc-intermediate peptide.

(1) The Fmoc-intermediate peptide is deprotected and neutralized, then washed with CH$_2$Cl$_2$ (3×1 min) and DMF (3×1 min).

(2) The Fmoc-amino acid is coupled to the deprotected intermediate peptide by: i) adding Fmoc amino acid (3 equiv.) and HOBt (3.3 equiv.)in DMF (3 min) to the intermediate peptide; ii) adding 3 equiv. DIC (as 20% solution in CH$_2$Cl$_2$) and shaking the mixture for 90 min.

(3) The mixture is then washed with ethanol (3×1 min) and DMF (3×1 min).

In order to couple further residues, the newly coupled Fmoc-amino acid is deprotected with 50% piperidine in DMF for 30 min, and washed with DMF (6×1 min). Other couplings follow as described at step (2).

Each time a new amino acid is coupled to the resin or peptide, a Kaiser test is performed; in case of incomplete coupling occurs, the reaction is repeated.

For the coupling of Fmoc-Gly and Fmoc-Gln, step (2) of this Operation is modified as follows: 3 equiv. DIC (as 20% $CH_2Cl_2$) is added to a mixture DMF solution of Fmoc amino acid (3.0 equiv.) and HOBt (3.3 equiv.) at 0° C. for 15 min and at room temperature 15. The reaction mixture is added to peptide resin, shaken for 1 hour if Fmoc-Gly and for 2 hours if Fmoc-Gln.

B) Using Boc-amino acid

The following procedures are performed for introducing a Boc-amino acid to an Fmoc-intermediate peptide.

(1) The Boc group is removed by adding 50% TFA in $CH_2Cl_2$;

(2) adding 50% TFA in $CH_2Cl_2$ containing 5% mercaptoethanol and 5% anisole for 25 minutes; and (3) washing with $CH_2Cl_2$ (2 times 1 min), MeOH (2 times 1 min), and DMF (3 times 1 min).

(4) Coupling of the Boc-amino acid residue is performed by adding 3 equivalents of Boc-amino acid and 3.3 equivalents HOBt in DMF and mixing for 3 minutes. Then 3 equivalents of 20% diisopropylcarbodiimide in $CH_2Cl_2$ are added and shaken for 90 minutes. The reaction mixture is then washed with MeOH (3 times 1 minute) and then $CH_2Cl_2$ (3 times 1 minute).

(5) The Boc group is removed (deprotection) by washing the product of step (5) with 50% TFA in $CH_2Cl_2$ containing 5% mercaptoethanol (5 minutes) and anisole (25 minutes). Further washes in $CH_2Cl_2$ (2 times 1 minute), MeOH (2 times 1 minute) and DMF (3 times 1 minute) follow.

It should be kept in mind that removal of the Boc group also removes the But protecting group suitably coupled to the $A^9$ side chain. Thus, removal of Boc is usually not performed until just before cyclization of the $A^9$ residue.

Operation 5: Formation of 5-membered heterocyclic ring

The ring structure of Formula IIA is formed by shaking the intermediate peptide having deprotected $Cys^9$ in a mixture of 50% AcOH, 3.7% HCHO and DMF (1:1:8) at room temperature for 3 minutes and filtered. The product is washed with DMF, MeOH and $CH_2Cl_2$ three times each.

The ring structure of Formula IIB is formed by shaking the intermediate with peptide having deprotected $Cys^9$ in a mixture of 50% AcOH, 10% $CH_3CHO$ and DMF (1.5:0.5:8) at room temperature for 10 minutes and filtered. The product is washed with DMF, MeOH and $CH_2Cl_2$ three times each.

The ring structure of Formula IIC is formed by shaking the intermediate with peptide having deprotected $Pen^9$ in a mixture of 50% AcOH, 3.7% HCHO and DMF (1:1:8) at room temperature for 10 minutes and filtered. The product is washed with DMF, MeOH and $CH_2Cl_2$ three times each.

Operation 6: Detachment of peptide from resin

After all the desired amino acid residues have been added, the intermediate peptide resin is treated with liquid HF in the presence of anisole to cleave the polypeptide from the support phase. This reaction removes side chain protecting groups as well. When BHA resin is used, the resulting intermediate peptide has $Q=NH_2$.

If X is other than H, the X group is placed at the N-terminal either by introducing an amino acid already bearing an X group (e.g., Ac-D-Phe); or by reacting the deprotected alpha amino group at the N-terminal $A^1$ of the intermediate pseudopeptide with a suitable reagent. Thus, a complete peptide once removed from the resin support phase may suitably be reacted with KOCN to yield $X=NH_2CO—$.

Operation 7: Purification of Peptides

The pseudopeptides of Formula I are generally purified by high performance liquid chromatography (HPLC) on a reversed phase column carried out on a Rainin HPLC System (Rainin Inc., Co., Woburn, Mass.) consisting of three Rainin Rabbit HP HPLC pumps controlled by an Apple Macintosh Plus computer, a Rheodyne Injector and a Knauer Model 87 variable wavelength UV monitor. Crude peptides (10–40 mg) are loaded on a Dynamax Macro column (21.2×250 mm) packed with spherical $C_{18}$ silica gel (pore size: 300A; particle size: 12 μm) (Rainin Inc. Co.) and eluted with linear gradient by using a solvent system consisting of (A) 0.1% TFA and (B) 0.1% TFA in 70% aqueous acetonitrile at a flow rate of 2.0 ml/min. All fractions are assessed for purity and retention time by an Analytical HPLC described at below.

The quality and the elution characteristics of crude and purified peptide are established by analytical HPLC on a Hewlett-Packard Model 1090 liquid chromatography equipped with a diode array detector set at 220 and 280 nm and a reversed phase 4.6×250 mm W-porex $C_{18}$ column (pore size: 300A, particle size: 5 μm). A flow rate of 1.2 ml/min of solvent system (A) and (B) described as above is maintained and the separations were performed at room temperature.

In most cases, pseudopeptide bombesin antagonists were further purified by rechromatography on the same column with slight modification to the gradient conditions. The homogeneity of purified peptides proved to be pure over 97% in analytical HPLC.

If desired, amino acid analysis of the pseudopeptides of Formula I may be performed in a Beckmann 6300 amino acid analyzer, on samples hydrolyzed at 110° C. for 20 hrs. in sealed, evacuated tubes with 4M methanesulfonic acid containing 0.2% 3-(2-aminoethyl)-indole.

C. SYNTHETIC INTERMEDIATES

1. Side Chain Protecting Groups

In solid phase synthesis, it is common to protect reactive side chain functional groups of the various amino acid moieties or peptide fragments. These side chain functional groups may be protected in order to prevent an undesirable chemical reaction from occurring at said chains. Accordingly, it is common that an intermediate peptide is produced which includes each of the amino acyl residues located in its desired sequence in the peptide chain with side-chain protecting groups linked to the appropriate residues.

In selecting a particular side chain protecting group to be used in the synthesis of the peptides, these rules are generally followed: (a) the protecting group preferably retains its protecting properties under coupling conditions, (b) the protecting group should be stable to the coupling reagents, is preferably stable under the coupling reaction conditions selected for removing the alpha amino protecting group at each step of the synthesis and, (c) the side chain protecting group must be removable upon the completion of the synthesis of the desired amino acid sequence, under reaction conditions that will not undesirably alter the peptide chain.

The side chain protecting groups are attached to the amino acid residues by steps well known in the art. Suitable side chain protecting groups for His include Bom; and for Glu and Cys include But.

2. Synthetic Intermediates

Also considered to be within the scope of the present invention are intermediate peptides at the following stages of synthesis. Illustrated here are intermediate peptides of Peptide 2 at three stages:

Stage A: following linkage of all the amino acids and the resin:
Boc-D-Phe-Gln-Trp-Ala-Val-Gly-His(Bom)-Leu-$psi$-Cys(But)-BHA resin ("1/02/A");

Stage B: following removal of the N-terminal Boc-group:
D-Phe-Gln-Trp-Ala-Val-Gly-His(Bom)-Leu-$psi$-Cys-BHA resin ("1/02/B");

Stage C: following cyclization of A$^9$:
D-Phe-Gln-Trp-Ala-Val-Gly-His(Bom)-Leu-$psi$-Tac-BHA resin ("1/02/C").

There is one further stage, Stage D, illustrated in the synthesis of Peptide No. 17 in Example 2 below. The Stage D intermediate is removed from the resin but does not yet have the single bond X, linking A$^1$ to A$^2$.

Medical Applications

The bombesin antagonists are useful for the treatment of states of hypergastrinemia, for example, pernicious anemia, chronic atrophic gastritis, Zollinger-Ellison Syndrome, and vitiligo, associated with diffuse hyperplasia of gastric enterochromaffin-like cells, and with an increased risk of developing, multifocal gastric carcinoid tumors. Furthermore, enterochromaffin-like cell hyperplasia is readily produced in animals rendered hypergastrinemic.

Such treatment is advantageous over present drugs, since H$_2$-antagonists like cimetidine which cause hypergastrinemia and may lead to carcinoid tumors in humans. In addition, cessation of therapy with H$_2$-antagonists causes an immediate recurrence of ulcers, because of existing hypergastrinemia.

Since these compounds of this invention are antagonists of bombesin/GRP receptors, they can be used in treatment of lung cancer, colon cancer and gastric cancer.

The Formula I bombesin antagonists of the invention may be administered in the form of pharmaceutically acceptable nontoxic acids or salts, such as acid addition salts, Illustrative of such acid addition salts are hydrochloride, hydrobromide, sulphate, phosphate, fumarate, gluconate, tannate, maleate, acetate, citrate, benzoate, succinate, alginate, pamoate, malate, ascorbate, tartrate, and the like.

These pharmaceutical compositions will contain the Formula I pseudopeptides in conjunction with a conventional, pharmaceutically-acceptable carrier, e.g., physiological saline being acceptable, though other carriers known to the art may be used.

Treatment of subjects with these pharmaceutical compositions may be carried out in the same manner as the clinical treatment using other agonists and antagonists of LHRH, or somatostatin analogues. Thus, the Formula I bombesin antagonists may be administered intravenously, subcutaneously, intramuscularly, intranasally or by pulmonary aerosol or in a depot form (e.g. microcapsules, microgranules or cylindrical rod-like implants) formulated from a biodegradable suitable polymer (such as DL-lactide-coglycolide). Other equivalent modes of administration are also within the scope of this invention, i.e., continuous drip, infusion pump and time-release modes, such as microcapsules and the like.

Effective dosages of Formula I peptides will vary with the form of administration and the particular species of mammal being treated. The dosage will be from about 1 to 1000 micrograms of the peptide per kilogram of the body weight of the host per day when given parenterally. These dosage ranges are merely preferred and higher dosages may be chosen in appropriate circumstances. A physiological saline solution containing the peptide may be administered to provide a dose in the range of about 0.01 to 0.20 mg/kg of body weight per day, except for depot forms where the amount injected is to be calculated to last from about 15 to about 30 days or longer.

In the following Examples, a three character code is utilized to identify intermediate peptides at certain stages of synthesis. A peptide encoded "1/01/A" is the intermediate peptide for Peptide "01" made in Example "1" which has completed Stage A in synthesis. Similarly, "2/08/B" and "4/19/C" are intermediate peptides of Peptides "08" and "19" in Examples 2 and 4 which have completed synthesis Stages B and C respectively.

Example (1)

| Peptide # | | |
|---|---|---|
| 1. | D—pGlu—Gln—Trp—Ala—Val—Gly—His—Leu-psi-Tac—NH$_2$ | Seq ID No. 1 |
| 2. | D—Phe—Gln—Trp—Ala—Val—Gly—His—Leu-psi-Tac—NH$_2$ | Seq ID No. 2 |
| 4. | Ac—D—Phe—Gln—Trp—Ala—Val—Gly—His—Leu-psi-Tac—NH$_2$ | Seq ID No. 4 |
| 5. | D—Cpa—Gln—Trp—Ala—Val—Gly—His—Leu-psi-Tac—NH$_2$ | Seq ID No. 5 |
| 7. | D—Nal—Gln—Trp—Ala—Val—Gly—His—Leu-psi-Tac—NH$_2$ | Seq ID No. 7 |
| 8. | Pal—Gln—Trp—Ala—Val—Gly—His—Leu-psi-Tac—NH$_2$ | Seq ID No. 8 |
| 9. | D—Pal—Gln—Trp—Ala—Val—Gly—His—Leu-psi-Tac—NH$_2$ | Seq ID No. 9 |
| 10. | D—Trp—Gln—Trp—Ala—Val—Gly—His—Leu-psi-Tac—NH$_2$ | Seq ID No. 10 |
| 11. | Ac—D—Trp—Gln—Trp—Ala—Val—Gly—His—Leu-psi-Tac—NH$_2$ | Seq ID No. 11 |
| 12. | Tpi—Gln—Trp—Ala—Val—Gly—His—Leu-psi-Tac—NH$_2$ | Seq ID No. 12 |
| 13. | D—Tpi—Gln—Trp—Ala—Val—Gly—His—Leu-psi-Tac—NH$_2$ | Seq ID No. 13 |

| Peptide # | | |
|---|---|---|
| 14. | Hca—Gln—Trp—Ala—Val—Gly—His—Leu-psi-Tac—NH₂ | Seq ID No. 14 |

These peptides may suitably be synthesized from a common intermediate I-1, Fmoc-Trp-Ala-Val-Gly-His(Bom)-Leu-*psi*-Cys(But)-BHA resin, and are synthesized as follows.

Fmoc-Leu-*psi*-Cys(But)-BHA resin is obtained as follows: 2.0 g BHA resin (0.55 mmol NH₂/g) is prepared by treatment with 20 ml 10% TEA in CH₂Cl₂ (neutralization) twice each for 3 minutes and washed with 20 ml CH₂Cl₂ six times; then mixed with 3.3 mmole Fmoc-Cys(But) and 3.6 mmole HOBt in DMF for three minutes. 3 equiv. DIC (as 20% solution in CH₂Cl₂) is added. The mixture is shaken at room temperature for 90 minutes. The resulting Fmoc-Cys(But)-BHA resin is washed with CH₂Cl₂, methanol two times each, and CH₂Cl₂ three times, and then subjected to a Kaiser test.

The coupling of Fmoc-Leu-CHO to form the pseudopeptide bond is performed as follows. The deprotection of Fmoc group from A⁹ is performed by adding 15 ml 50% piperidine in DMF and mixing for 30 min and washing with 15 ml DMF (6×1 min). Then 3.3 mmole Fmoc-Leu-CH (3 equiv.)in DMF containing 1% AcOH is added, followed by NaBH₃CN (3.5 equiv.) in DMF and shaking 1 hour. This is followed by washing with 15 ml 50% MeOH (3×1 min); 15 ml 100% MeOH (3×1 min); and 15 ml DMF (3×1 min).

The removal of the Fmoc-group (deprotection) from Fmoc-Leu-*psi*-Cys(But)-BHA resin is carried out per Operation 4A.

After the removal of the Fmoc group from Fmoc-Leu-*psi*-Cys(But)-BHA resin and neutralization, the coupling of Fmoc-His(Bom) is carried out as described in Operation 4A.

The coupling of Fmoc-Gly is performed as in Operation 4. 20% 1,3-diisopropylcarbodiimide (3.3 mmole) in CH₂Cl₂ was added to a DMF solution of 3.3 mmoles Fmoc-Gly and 3.6 mmoles HOBt at 0° C., stirred under cooling for 15 min and at room temperature for 15 min, the precipitate filtered off and added to resin, and shaken for 60 min. The subsequent amino acid residues Fmoc-Val, Fmoc-Ala and Fmoc-Trp are then sequentially introduced by coupling in the same manner to yield 3.80 g of intermediate I-1, the protected peptide resin with structure Fmoc-Trp-Ala-Val-Gly-His(Bom)-Leu-*psi*-Cys(But)-BHA resin.

Sequential coupling of Fmoc-Gln and Boc-D-pGlu to intermediate peptide I-1 yields: Boc-D-pGlu-Gln-Trp-Ala-Val-Gly-His(Bom)-Leu-*psi*-Cys(But)-BHA resin ("1/01/A").

Sequential coupling of Fmoc-Gln and Boc-D-Phe to intermediate peptide I-1 yields: Boc-D-Phe-Gln-Trp-Ala-Val-Gly-His(Bom)-Leu-*psi*-Cys(But)-BHA resin ("1/02/A").

Sequential coupling of Fmoc-Gln and Ac-D-Phe to intermediate peptide I- 1 yields: Ac-D-Phe-Gln-Trp-Ala-Val-Gly-His(Bom)-Leu-*psi*-Cys(But)-BHA resin ("1/04/A ").

Sequential coupling of Fmoc-Gln and Boc-D-Cpa to intermediate peptide I-1 yields: Boc-D-Cpa-Gln-Trp-Ala-Val-Gly-His(Bom)-Leu-*psi*-Cys(But)-BHA resin ("1/05/A").

Sequential coupling of Fmoc-Gln and Boc-D-Nal to intermediate peptide I-1 yields: Boc-D-Nal-Gln-Trp-Ala-Val-Gly-His(Bom)-Leu-*psi*-Cys(But)-BHA resin ("1/07/A").

Sequential coupling of Fmoc-Gln and Boc-Pal to intermediate peptide I-1 yields: Boc-Pal-Gln-Trp-Ala-Val-Gly-His(Bom)-Leu-*psi*-Cys(But)-BHA resin ("1/08/A").

Sequential coupling of Fmoc-Gln and Boc-D-Pal to intermediate peptide I-1 yields: Boc-D-Pal-Gln-Trp-Ala-Val-Gly-His(Bom)-Leu-*psi*-Cys(But)-BHA resin ("1/09/A").

Sequential coupling of Fmoc-Gln and Boc-D-Trp to intermediate peptide I-1 yields: Boc-D-Trp-Gln-Trp-Ala-Val-Gly-His(Bom)-Leu-*psi*-Cys(But)-BHA resin ("1/10/A").

Sequential coupling of Fmoc-Gln and Ac-D-Trp to intermediate peptide I-1 yields: Ac-D-TrP-Gln-Trp-Ala-Val-Gly-His(Bom)-Leu-*psi*-Cys(But)-BHA resin ("1/11/A").

Sequential coupling of Fmoc-Gln and Boc-Tpi to intermediate peptide I-1 yields: Boc-Tpi-Gln-Trp-Ala-Val-Gly-His(Bom)-Leu-*psi*-Cys(But)-BHA resin ("1/12/A").

Sequential coupling of Fmoc-Gln and Boc-D-Tpi to intermediate peptide I-1 yields: Boc-D-Tpi-Gln-Trp-Ala-Val-Gly-His(Bom)-Leu-*psi*-Cys(But)-BHA resin ("1/13/A").

Sequential coupling of Fmoc-Gln and Hca to intermediate peptide I-1 yields: Hca-Gln-Trp-Ala-Val-Gly-His(Bom)-Leu-*psi*-Cys(But)-BHA resin ("1/14/A").

The N-terminal Boc group of intermediate peptide 1/01/A is then removed by treatment with 50% TFA in CH₂Cl₂ containing 5% mercaptoethanol and 5% anisole twice, first for 5 minutes and then for 25 minutes. The intermediate peptide is then washed with CH₂Cl₂ (2 times 1 min), MeOH (2 times 1 min) and DMF (3 times 1 min). This also removes the But protecting group from Cys, producing intermediate peptide D-pGlu-Gln-Trp-Ala-Val-Gly-His(Bom)-Leu-*psi*-Cys-BHA resin ("1/01/B"), which is then washed with CH₂Cl₂, MeOH and DMF, three times each for one minute.

At this point, the Cys side chain of intermediate peptide 1/01/B is cyclized by oxidation to form the 5-membered heterocyclic ring shown in Formula IIA per Operation 5. A 10 ml mixture of AcOH, 3.7% HCHO and DMF (1:1:8) is added. The reaction mixture is shaken at room temperature for 3 minutes, washed with water, DMF and CH₂Cl₂ 3 times each to yield intermediate peptide 1/01/C, D-pGlu-Gln-Trp-Ala-Val-Gly-His(Bom)-Leu-*psi*-Tac-BHA resin.

Intermediate peptide 1/01/C is then treated with HF and anisole per Operation 6 to remove the Bom protecting group from His and simultaneously cleave the nonapeptide from the resin support phase resulting in a C-terminal Q group which is —NH₂. The peptide is purified with HPLC per Operation 7. The bombesin antagonist peptide number 1 is thus obtained.

The same steps of removing the Boc group and But group and cyclizing the —CH₂—SH group of Cys with the secondary amine of the reduced bond are performed on intermediate peptides 1/02/A, 1/05/A, 1/07/A, 1/08/A, 1/09/A, 1/10/A and 1/12/A to yield intermediate peptides as follows:

| | |
|---|---|
| 1/02/B | D—Phe—Gln—Trp—Ala—Val—Gly—His(Bom)—Leu-psi-Tac—BHA resin |
| 1/04/B | Ac—D—Phe—Gln—Trp—Ala—Val—Gly—His(Bom)—Leu-psi-Tac—BHA resin |
| 1/05/B | D—Cpa—Gln—Trp—Ala—Val—Gly—His(Bom)—Leu-psi-Tac—BHA resin |
| 1/07/B | D—Nal—Gln—Trp—Ala—Val—Gly—His(Bom)—Leu-psi-Tac—BHA resin |
| 1/08/B | Pal—Gln—Trp—Ala—Val—Gly—His(Bom)—Leu-psi-Tac—BHA resin |
| 1/09/B | D—Pal—Gln—Trp—Ala—Val—Gly—His(Bom)—Leu-psi-Tac—BHA resin |
| 1/10/B | D—Trp—Gln—Trp—Ala—Val—Gly—His(Bom)—Leu-psi-Tac—BHA resin |
| 1/11/B | Ac—D—Trp—Gln—Trp—Ala—Val—Gly—His(Bom)—Leu-psi-Tac—BHA resin |
| 1/12/B | Tpi—Gln—Trp—Ala—Val—Gly—His(Bom)—Leu-psi-Tac—BHA resin |
| 1/13/B | D—Tpi—Gln—Trp—Ala—Val—Gly—His(Bom)—Leu-psi-Tac—BHA resin |
| 1/14/B | HCa—Gln—Trp—Ala—Val—Gly—His(Bom)—Leu-psi-Tac—BHA resin |

The crude peptides are cleaved from BHA resin, and then purified by Operation 6 and 7 to yield pure peptides 2, 4, 5, and 7–14.

The retention time of these peptides is as follows.

| Analytical HPLC data | | |
|---|---|---|
| Peptide No. | Gradient % B/min | Retention time on Column D |
| 1 | 25–65 | 14.40 |
| 2 | 25–65 | 14.20 |
| 3 | 25–75 | 15.17 |
| 5 | 25–65 | 16.11 |
| 7 | 20–60 | 23.75 |
| 8 | 20–60 | 13.19 |
| 9 | 25–65 | 12.00 |
| 10 | 25–65 | 16.98 |
| 11 | 25–65 | 24.50 |
| 12 | 25–65 | 19.91 |
| 13 | 25–65 | 16.99 |
| 14 | 40–80 | 13.68 |

Alternatively, the 5-membered heterocyclic ring may be formed in a solution with the procedure as follows:

25 mg of an intermediate peptide including the structure Leu-$_{psi}$-Cys-NH$_2$, obtained from solid phase synthesis in 0.8 ml glacial acetic acid is mixed with 100 ul 1% formaldehyde (wt % solution in water) at room temperature for 30 seconds, and then 20 ul 50% ammonium acetate solution is added. The reaction mixture is subjected purification to yield the desired peptide which contains the structure -Leu-$_{psi}$-Tac-NH$_2$.

EXAMPLE (2)

(1). A 150 mg portion of intermediate I-2 is then divided into 3 aliquots and subjected to two further couplings with the procedure described in Operation 4 to yield the final nonapeptide resins.

Sequential coupling of Fmoc-His(Bom) and Boc-D-Phe to intermediate peptide I-2 yields: Boc-D-Phe-His(-Bom)-Trp-Ala-Val-Gly-His(Bom)-Leu-$_{psi}$-Cys(But)-BHA resin ("2/15/A").

Sequential coupling of Fmoc-Glu(OMe) and Boc-D-Phe to intermediate peptide I-2 yields Boc-D-Phe-Glu(OMe)-Trp-Ala-Val-Gly-His(Bom)-Leu-$_{psi}$-Cys(-But)-BHA resin ("2/16/A").

Sequential coupling of Fmoc-Glu(But) and Boc-D-Phe to intermediate peptide I-2 yields: Boc-D-Phe-Glu(-But)-Trp-Ala-Val-Gly-His(Bom)-Leu-$_{psi}$-Cys(But)-BHA resin ("2/17/A").

The removal of Boc-group from intermediate peptide 2/15/A is performed using 50% TFA in CH$_2$Cl$_2$ containing 5% mercaptoethanol and 5% anisole per Operation 4. This reaction also removes the But group from residue A$^9$, resulting in intermediate peptide 2/15/B:
  D-Phe-His(Bom)-Trp-Ala-Val-Gly-His(Bom)-Leu-$_{psi}$-Cys-BHA resin.

At this point, the Cys side chain of intermediate peptide 2/15/B is cyclized by oxidation to form the 5-membered heterocyclic ring shown in Formula IIA per Operation 5. A 10 ml mixture of AcOH, 3.7% HCHO and DMF (1:1:8) is added. The reaction mixture is shaken at room temperature for 3 minutes, washed with water, DMF and CH$_2$Cl$_2$ 3 times each to yield intermediate peptide 2/15/C:
  D-Phe-His(Bom)-Trp-Ala-Val-Gly-His(Bom)-Leu-$_{psi}$-Tac-BHA resin.

| Peptide # | | |
|---|---|---|
| 15. | D—Phe—His—Trp—Ala—Val—Gly—His—Leu-psi-Tac—NH$_2$ | Seq ID No. 15 |
| 16. | D—Phe—Glu(OMe)—Trp—Ala—Val—Gly—His—Leu-psi-Tac—NH$_2$ | Seq ID No. 16 |
| 17. | ┌─────────┐<br>└─D—Phe—Glu[-]—Trp—Ala—Val—Gly—His—Leu-psi-Tac—NH$_2$ | Seq ID No. 17 |

The peptides in this example may suitably be synthesized from the common intermediate I-2, Fmoc-Trp-Ala-Val-Gly-His(Bom)-Leu-$_{psi}$-Cys(But)-BHA resin, built step by step on 0.5 g BHA resin (0.55 mmoles NH2/g). Intermediate peptide I-2 is prepared according to the Operations and procedures set out in Example Then, intermediate peptide 2/15/C is treated with freshly distilled HF (5 ml) and anisole (0.25 ml) at 0° C. for 1 hour, thereby also removing the Bom protecting group from His. The solvent is evaporated in vacuo and washed with ethyl acetate, extracted with 70–80% aqueous acetic acid and lyophilized. After purification, bombesin antagonist peptide number 15 is obtained.

The same steps to remove the N-terminal Boc, cyclize Cys⁹, remove the intermediate peptide from BHA resin and purify with HPLC are performed on intermediate peptides 2/16/A and 2/17/A to yield peptide number 16 and intermediate peptide 2/17/D: D-Phe-Glu-Trp-Ala-Val-Gly-His-Leu-$_{psi}$-Tac-NH$_2$.

A mixture of 15 mg of 2/17/D, and 15 mg HOBt in 0.8 ml DMF at 0° C. is added to 50 microliters 25% diisopropyl carbodiimide in CH$_2$Cl$_2$ and stirred at 0° C. for 2 hours. The single bond of peptide 17 linking the alpha amino of D-Phe¹ to the gamma carboxyl moiety on the 3-propionyl moiety of Glu² is formed:

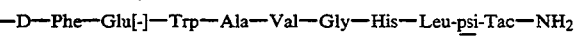

D—Phe—Glu[-]—Trp—Ala—Val—Gly—His—Leu-psi-Tac—NH$_2$

The reaction mixture is subjected to purification with HPLC in accordance with Operation 7.

The retention times of these peptides are as follows.

| | Analytical HPLC data | |
|---|---|---|
| Peptide No. | Gradient % B/min | Retention time on Column D |
| 15 | 20–60 | 17.23 |
| 16 | 25–65 | 19.13 |
| 17 | 20–60 | 20.34 |

EXAMPLE (3)

| Peptide # | | |
|---|---|---|
| 3. | D—Phe—Gln—Trp—Ala—Val—Gly—His—Leu-psi-MTac—NH$_2$ | Seq ID No. 3 |
| 6. | D—Cpa—Gln—Trp—Ala—Val—Gly—His—Leu-psi-MTac—NH$_2$ | Seq ID No. 6 |

These bombesin antagonists may suitably be synthesized from a common intermediate I-3, i.e., Fmoc-Gln-Trp-Ala-Val-Gly-His(Bom)-Leu-$_{psi}$-Cys(But)-BHA resin. This is built on 1.0 g. BHA resin (0.55 m moles NH$_2$/g) by the successive coupling with solid phase synthesis operations as described at Example (1) beginning with Fmoc-Cys(But) and followed by Fmoc-Leu-CH (with NaBH$_3$CN); and Fmoc-His(Bom), etc. further according to Example (1). Fmoc-Gln is linked to the N terminal according to Operation 4 to form the Intermediate I-3. The final coupling of Boc-D-Phe or Boc-D-Cpa to Intermediate I-3, is performed according to the procedure in Operation 4 to form intermediate peptides "3/3/A" or "3/6/A" respectively.

The removal of Boc group is performed using 50% TFA in CH$_2$Cl$_2$ containing 5% mercaptoethanol and 5% anisole per Operation 4.

At this point, the Cys side chain of intermediate peptide 3/3/B is cyclized by oxidation to form the 5-membered heterocyclic ring shown in Formula IIB per Operation 5. A 10 ml mixture of 50% AcOH, 10% CH$_3$CHO and DMF (1.5:0.5:8) is added. The reaction mixture is shaken at room temperature for 10 minutes, washed with water, DMF and CH$_2$Cl$_2$ 3 times each to yield intermediate peptide 3/3/C: D-Phe-Gln-Trp-Ala-Val-Gly-His-Leu-$_{psi}$-MTac-BHA resin.

Intermediate peptides 3/3/C and 3/6/C are removed from the resin per Operation 6 by treatment with HF (5 ml) and anisole (0.25 ml) at 0° C for 1 hour. This process also removes the Bom protecting group from His, yielding final nonapeptides 3 and 6.

The peptides are purified with HPLC per Operation 7; their retention times are as follows.

Seq ID No. 17

| | Analytical HPLC data | |
|---|---|---|
| Peptide No. | Gradient % B/min | Retention time on Column D |
| 3 | 25–65 | 15.71 |
| 6 | 25–65 | 17.37 |

Alternatively, the 5-membered heterocyclic ring may be formed in a solution by adding to 25 mg an intermediate peptide containing the structure of Leu-$_{psi}$-Cys-NH$_2$, 0.8 ml glacial acetic acid is mixed with 100 microliters 10% acetaldehyde at room temperature. This is mixed for 5 minutes; then 100 microliters ammonium acetate are added. The reaction mixture is subjected to purification to yield a desired peptide which contains the structure of Leu-$_{psi}$-MTac-NH$_2$.

EXAMPLE (4)

| Peptide # | | |
|---|---|---|
| 18. | D—Phe—Gln—Trp—Ala—Val—Gly—His—Leu-psi-DMTac—NH$_2$ | Seq ID No. 18 |
| 19. | Ac—D—Phe—Gln—Trp—Ala—Val—Gly—His—Leu-psi-DMTac | Seq ID No. 19 |
| 20. | D—Cpa—Gln—Trp—Ala—Val—Gly—His—Leu-psi-DMTac—NH$_2$ | Seq ID No. 20 |
| 21. | Tpi—Gln—Trp—Ala—Val—Gly—His—Leu-psi-DMTac—NH$_2$ | Seq ID No. 21 |
| 22. | D—Tpi—Gln—Trp—Ala—Val—Gly—His—Leu-psi-DMTac—NH$_2$ | Seq ID No. 22 |

These polypeptides may suitably be synthesized from a common intermediate I-4, Fmoc-Trp-Ala-Val-Gly-His(Bom)-Leu-$_{psi}$-Pen(But)-BHA resin. This intermediate is built step by step on benzhydrylamine (BHA) resin in accordance with the standard methods of solid phase synthesis as described in Examples (1) and (2).

Thus, 1.0 g BHA resin (0.55 mmole NH$_2$/g)is prepared according to Operation 2, being treated with 10 ml 10% TEA in CH$_2$Cl$_2$ (neutralization) twice each for three minutes and washed with 10 ml CH$_2$Cl$_2$ six times; then mixed with 1.6 mmole Fmoc-Pen(But) and 1.8 mmoles 1-hydroxybenzotriazole (HOBt) in DMF for three minutes. 20% 1,3-diisopropylcarbodiimide (DIC) with 1.6 mmoles in CH$_2$Cl$_2$ is added. The mixture is shaken at room temperature for 90 minutes. The resulting Fmoc-Pen(But)-BHA resin is washed with CH$_2$Cl$_2$, methanol two times each, and $CH_2Cl_2$ three times, and then subjected to a Kaiser test.

The removal of the Fmoc-group (deprotection) from Fmoc-Pen(But)-BHA resin is carried out per operation 4A.

The coupling of Fmoc-Leu-CHO is performed according to Operation 3. The $A^9$(But)-BHA resin is washed with DMF 2 times. Then 1.6 mmoles Fmoc-Leu-CHO in DMF containing 1% AcOH is added, followed by 1.8 mmoles $NaBH_3CN$ in DMF. The reaction mixture is shaken for 60 minutes, then washed with 50% methanol in $H_2O$ 2 times, 100% MeOH 2 times, and $CH_2Cl_2$ 3 times, each for 1 minute.

After the removal of the Fmoc group from Fmoc-Leu-$psi$-Pen(But)-BHA resin and neutralization, the coupling of Fmoc-His(Bom) is carried out as described as in Operation 4.

The coupling of Fmoc-Gly is performed as in Operation 4. 20% 1,3-diisopropylcarbodiimide (1.5 mmole) in $CH_2Cl_2$ was added to a DMF solution of 1.5 mmoles Fmoc-Gly and 1.65 mmoles HOBt at 0° C., stirred under cooling for 15 min and at room temperature for 15 min, the precipitate filtered off and added to resin, and shaken for 60 min. The subsequent amino acid residues Fmoc-Val, Fmoc-Ala and Fmoc-Trp are then sequentially introduced by coupling in the same manner to yield 1.9 g of intermediate I-4, the protected peptide resin with structure Fmoc-Trp-Ala-Val-Gly-His(Bom)-Leu-$psi$-Pen(But)-BHA resin.

0.91 g of intermediate I-4 is divided into five aliquots (about 200 mg each) which are used to synthesize protected polypeptide resins in accordance with the procedures described at Operation 4:

Sequential coupling of Fmoc-Gln and Boc-D-Phe to intermediate peptide I-4 yields: Boc-D-Phe-Gln-Trp-Ala-Val-Gly-His(Bom)-Leu-$psi$-Pen(But)-BHA resin ("4/18/A").

Sequential coupling of Fmoc-Gln followed by Ac-D-Phe to intermediate peptide I-4 yields: Ac-D-Phe-Gln-Trp-Ala-Val-Gly-His(Bom)-Leu-$psi$-Pen(But)-BHA resin ("4/19/A").

Sequential coupling of Fmoc-Gln and Boc-D-Cpa to intermediate peptide I-4 yields: Boc-D-Cpa-Gln-Trp-Ala-Val-Gly-His(Bom)-Leu-$psi$-Pen(But)-BHA resin ("4/20/A").

Sequential coupling of Fmoc-Gln followed by Boc-Tpi to intermediate peptide I-4 yields: Boc-Tpi-Gln-Trp-Ala-Val-Gly-His(Bom)-Leu-$psi$-Pen(But)-BHA resin ("4/21/A").

Sequential coupling of Fmoc-Gln followed by Boc-Tpi to intermediate peptide I-4 yields: Boc-D-Tpi-Gln-Trp-Ala-Val-Gly-His(Bom)-Leu-$psi$-Pen(But)-BHA resin ("4/22/A").

The Boc-group is then removed from intermediate peptide 4/18/A with 50% TFA in $CH_2Cl_2$ containing 5% mercaptoethanol and 5% anisole, resulting in intermediate peptide 4/18/B: D-Phe-Gln-Trp-Ala-Val-Gly-His(Bom)-Leu-$psi$-Pen-BHA resin.

At this point, the Pen side chain of intermediate peptide 4/18B is cyclized by oxidation to form the 5-membered heterocyclic ring shown in Formula IIC per Operation 5. A 10 ml mixture of AcOH, 3.7% HCHO and DMF (1:1:8) is added to form a reaction mixture which is shaken at room temperature for 3 minutes, washed with water, DMF and $CH_2Cl_2$ 3 times each to yield intermediate peptide 4/18/C: D-Phe-Gln-Trp-Ala-Val-Gly-His(Bom)-Leu-$psi$-DMTac-BHA resin.

Intermediate peptide 4/18/C is then washed with 5 ml $CH_2Cl_2$, methanol and $CH_2Cl_2$ three times each and treated with freshly distilled HF (5 ml) and anisole (0.25 ml) at 0° C. for 1 hr. The solvent is evaporated in vacuo, washed with ether or ethylacetate then extracted with 70–80% acetic acid and lyophilized to yield crude nonapeptide resin. The reaction mixture is purified to yield bombesin antagonist peptide number 18.

The same steps for removing the protecting groups, cyclizing the deprotected $A^9$ and displacing the intermediate peptide from the BHA resin are performed on intermediate peptides 4/19/A, 4/20/A, 4/21/A, and 4/22/A to yield peptide numbers 19, 20, 21 and 22.

The purification is carried by HPLC with solvent system consisting of (A) 0.1% TFA and (B) 1% TFA in 70% acetonitrile in accordance with Operation 7. Purified peptides are proved to be over 97% pure in analytical HPLC. Retention time of these peptides follow.

| | Analytical HPLC data | |
|---|---|---|
| Peptide No. | Gradient % B/min | Retention time on Column D |
| 18 | 25–65 | 14.01 |
| 19 | 25–65 | 22.96 |
| 20 | 25–65 | 15.97 |
| 21 | 25–65 | 19.19 |
| 22 | 25–65 | 16.53 |

Alternatively, the $A^9$ residue may be cyclized in solution by adding 25 mg free peptide containing the structure -Leu-$psi$-Pen-$NH_2$ to 25 mg HOBt in 0.8 ml glacial acetic acid mixed with 100 microliters 10% formaldehyde and stirring at 0° C. for 30 minutes to yield the peptide having the 5-membered ring structure Leu-$psi$-DMTac-$NH_2$.

EXAMPLE (5)

Pal—Gln—Trp—Ala—Val—Gly—His—Leu-psi-Cys—$NH_2$

D—Pal—Gln—Trp—Ala—Val—Gly—His—Leu-psi-Cys—$NH_2$

Tpi—Gln—Trp—Ala—Val—Gly—His—Leu-psi-Cys—$NH_2$

D—Tpi—Gln—Trp—Ala—Val—Gly—His—Leu-psi-Cys—$NH_2$

Hca—Gln—Trp—Ala—Val—Gly—His—Leu-psi-Cys—$NH_2$

These peptides may be synthesized from a common intermediate I-5, Fmoc-Gln-Trp-Ala-Val-Gly-His(-Bom)-Leu-$psi$-Cys(But)-BHA resin.

Fmoc-Leu-$psi$-Cys(But)-BHA resin is obtained as follows: 1.0 g BHA resin (0.55 m mole $NH_2$/g) is coupled with Fmoc-Cys(But) and Fmoc-Leu-CHO successively by the method indicated in Operations 2 and 3.

Sequential coupling of Fmoc-His(Bom), Fmoc-Gly, Fmoc-Val, Fmoc-Ala and Fmoc-Trp and Fmoc-Gln results in Fmoc-Gln-Trp-Ala-Val-Gly-His(Bom)-Leu-$psi$-Cys(But)-BHA resin, intermediate peptide I-5.

A 150 mg. aliquot of this intermediate I-5 common to all peptides of this Example, is subjected to one further coupling with the procedures described in Operation 4 to yield the final peptide resins.

Sequential coupling of Boc-Pal to intermediate peptide I-5 yields: Boc-Pal-Gln-Trp-Ala-Val-Gly-His(Bom)-Leu-$psi$-Cys(But)-BHA resin ("5/08/A").

Sequential coupling of Boc-D-Pal to intermediate peptide I-5 yields: Boc-D-Pal-Gln-Trp-Ala-Val-Gly-His(Bom)-Leu-$psi$-Cys(But)-BHA resin ("5/09/A").

Sequential coupling of Boc-Tpi to intermediate peptide I-5 yields: Boc-Tpi-Gln-TrP-Ala-Val-Gly-His(Bom)-Leu-$_{psi}$-Cys(But)-BHA resin ("5/12/A").

Sequential coupling of Boc-D-Tpi to intermediate peptide I-5 yields: Boc-D-Tpi-Gln-Trp-Ala-Val-Gly-His(Bom)-Leu-$_{psi}$-Cys(But)-BHA resin ("5/13/A").

Sequential coupling of Hca to intermediate peptide I-5 yields: Hca-Gln-Trp-Ala-Val-Gly-His(Bom)-Leu-$_{psi}$-Cys(But)-BHA resin ("5/14/A").

The N-terminal Boc group is removed from intermediate peptide 5/01/A by treatment with 50% TFA in $CH_2Cl_2$ containing 5% mercaptoethanol and 5% anisole twice, first for 5 minutes and then for 25 minutes. This treatment removes the protecting group from Cys. The peptide is then washed with $CH_2Cl_2$, MeOH and DMF, per Operation 4, resulting in intermediate peptide 5/08/B: Pal-Gln-Trp-Ala-Val-Gly-His(Bom)-Leu-$_{psi}$-Cys-BHA resin.

Intermediate peptide 5/08/B is then treated with freshly distilled HF (5 ml) and anisole (0.25 ml) at 0° C. for 1 hour, also removing the Bom protecting group from His. The solvent is evaporated in vacuo and washed with ethylacetate, extracted with 70-80% acetic acid and lyophilized, yielding the following peptide: Pal-Gln-Trp-Ala-Val-Gly-His-Leu-$_{psi}$-Cys-$NH_2$.

The protecting group and BHA resin are removed from intermediate peptides 5/08/A, 5/09/A, 5/11/A, 5/12/A 5/13/A and 5/14/A to yield the peptides enumerated at the beginning of this Example. These are subjected to purity test in accordance with Operation 7.

| Analytical HPLC data | | |
|---|---|---|
| Peptide No. | Gradient % B/min | Retention time on column D |
| 5/08 | 20–60 | 5.56 |
| 5/09 | 25–65 | 4.60 |
| 5/12 | 25–65 | 12.78 |
| 5/13 | 25–65 | 9.62 |
| 5/14 | 40–80 | 7.39 |

Alternatively, these peptides may suitably be built step-by-step on BHA resin with Boc-protected amino acids and using Bz to protect the —SH group of $Cys^9$ in accordance with the standard methods of solid phase methods, resulting in intermediate peptides as follows:

cleave the peptide from the resin, also removing the protecting group Bom from His and Bz from Cys to yield the peptides enumerated at the beginning of this Example.

EXAMPLE (6): Assay Procedures (A) Receptor Binding Assay

Binding of $^{125}$I-$Tyr^4$-Bombesin and its displacement by bombesin antagonist pseudopeptides is tested in 24-well tissue culture plates (GIBCO) using Swiss 3T3 cells. Murine Swiss 3T3 fibroblasts are maintained by weekly passage in DMEM containing 10% FCBS and antimycotics. Cultures are incubated in 5% $CO_2$ in air at 37° C. The wells are seeded with $10^5$ cells/well (viability >95%), grown to confluence and quiescency. The binding procedure is conducted 7 days after seeding. The cells are washed 2 times with 0.5 ml of binding buffer (Dulbecco's modified Eagle's medium containing 20 nM HEPES-NaOH (pH 7.4), 0.2% BSA and 100 mcg/ml bacitracin). The cells are then incubated with 0.2 nM $^{125}$I-$Tyr^4$-Bombesin in the presence or absence of different concentrations of antagonists ($6 \times 10^{-11} - 6 \times 10^{-6}$M, total volume 0.4 ml).

The cells are incubated for 30 min at 37° C. since binding of $^{125}$I-GRP at 37° C. reaches a maximum value at 30 min and decreases afterwards, according to Zachary and Rozengurt (1985) and Layton et al., (1988). After that, the cells were washed 2 times with ice-cold (4 ° C.) binding buffer and 2 times with ice-cold phosphate-buffered saline (PBS,mM): NaCl 138, KCl 2.8, $Na_2HPO_4$ 8, $KH_2PO_4$ 1.45, $CaCl_2$ 0.91, $MgCl_2$ 0.49. Washed cultures are extracted in 0.5 ml of 0.5M NaOH and transferred to tubes for counting. The wells are washed once with 0.5 ml distilled water (sterile), and the washing is added to the appropriate tubes. Then the radioactivity of the samples is counted in an automatic gamma counter (Micromedic System, Inc., Huntsville, Ala.).

The Ligand-PC computerized curve fitting program of Munson and Rodbard is used to determine the types of receptor binding, dissociation constant (Kd), association constant (Ka), and the maximal binding capacity of receptors (Bmax).

The binding data of polypeptides in the present invention are listed on Table I below. Varying doses of unlabeled peptide were used to determine the ability to Boc—Pal—Gln—Trp—Ala—Val—Gly—His(Bom)—Leu-psi-Cys(Bz)—BHA resin ("5/08/A").
Boc—D—Pal—Gln—Trp—Ala—Val—Gly—His(Bom)—Leu-psi-Cys(Bz)—BHA resin ("5/09/A").
Boc—Tpi—Gln—Trp—Ala—Val—Gly—His(Bom)—Leu-psi-Cys(Bz)—BHA resin ("5/12/A").
Boc—D—Tpi—Gln—Trp—Ala—Val—Gly—His(Bom)—Leu-psi-Cys(Bz)—BHA resin ("5/13/A").
Hca—Gln—Trp—Ala—Val—Gly—His(Bom)—Leu-psi-Cys(Bz)—BHA resin ("5/14/A")

The Boc group is removed by treatment with 50% TFA in $CH_2Cl_2$ containing 5% mercaptoethanol and 5% anisole, and then treated with HF and anisole to displaced specific $^{125}$I-$Tyr^4$-Bombesin binding. The mean value of 2-3 independent tests for each peptide (each performed in triplicate) are indicated.

TABLE 1

| Inhibition of Binding of $^{125}$I—$Tyr^4$-Bombesin to Swiss 3T3 | |
|---|---|
| Peptide No. | Cells by Bombesin Antagonists $K_i$ [nM] |
| 01 | 5.0 |
| 02 | 0.078 |
| 03 | 13 |
| 04 | 13 |
| 05 | 0.007 |
| 06 | 4.3 |
| 07 | 0.009 |
| 08 | 4.5 |

TABLE 1-continued

Inhibition of Binding of $^{125}$I—Tyr$^4$-Bombesin to Swiss 3T3

| Peptide No. | Cells by Bombesin Antagonists $K_i$ [nM] |
|---|---|
| 09 | 8.8 |
| 10 | 0.11 |
| 11 | 5.4 |
| 12 | <0.001 |
| 13 | <0.001 |
| 14 | <0.001 |
| 15 | 0.26 |
| 16 | 12 |
| 17 | 213 |
| 18 | 0.93 |
| 19 | 20 |
| 20 | 13 |
| 21 | 0.07 |
| 22 | 0.074 |
| D—Tpi—Gln—Trp—Ala—Val—Gly—His—Leu-psi-Leu—NH$_2$ | 0.20 |
| Bombesin[b] | 0.28 |

[a]mean value of 6 tests;
[b]mean value of 11 tests.

EXAMPLE (7)

The effect of treatment with bombesin antagonists on tumor volume of estrogen independent MXT mouse mammary cancers is tested as follows: 40 female B6D2F$_1$ mice are obtained from the National Cancer Institute, Frederick Cancer Research Facility (Frederick, Md.) and housed at 21±1° C. and 55+5% humidity. The animals are kept under an automatic 12-H light/12-H darkness schedule and given rodent laboratory chow 50001 and tap water ad libitum. An estrogen independent MXT (3.2)/Ovex mammary carcinoma cryo-preserved tissue, obtained from Dr. A. E. Bogden (Biomeasure Inc., Hopkinton, Mass.) is inoculated into the mature female mice subcutaneously with one mm$^3$ of MXT (3.2)/Ovex tumor.

Two days after transplantation of the tumors, the mice are randomly divided into four groups and therapy with sustained delivery systems (microcapsules) of the peptides is initiated. The following four groups are established:

1) Control, injection vehicle only;
2) [D-Tpi$^6$, Leu$^{13}$-$_{psi}$-Leu$^{14}$] Bn(6-14),
3) [D-Phe$^6$, Leu$^{13}$-$_{psi}$-Tac$^{14}$] Bn(6-14),
4) Surgical bilateral ovariectomy.

These abbreviations for the bombesin antagonists employ conventional numbering for a residue of a peptide fragment: each residue is numbered according to the position it bears in the complete fragment. However, the bombesin antagonists are more easily compared to other peptides herein if numbered starting with "one" from the N-terminal. Thus, "[D-Tpi$^6$-Leu$^{13}$-$_{psi}$-Leu$^{14}$]Bn(6-14)" is D-Tpi$^1$-Gln$^2$-Trp$^3$-Ala$^4$-Val$^5$-Gly$^6$-His$^7$-Leu$^8$-$_{psi}$-Leu$^9$-NH$_2$ (hereinafter "B1"), while "[D-Phe$^6$-Leu$^{13}$-$_{psi}$-Tac$^{14}$]Bn(6-14)" is the same as Peptide No. 2 above.

The two bombesin antagonists are synthesized by solid phase methods. Group 2 of the mice received sustained release formulation of "B1", while group 3 received a formulation with Peptide No. 2 above. This sustained release formulation maintained a continuous liberation of B1 or Peptide No. 2 at 25 microgram/day for 15 days.

For sustained delivery, Alzet osmotic pumps (Alzo Co., Palo Alto, Calif.) were used. Alzet Pump Model 2002 releasing 0.48 μl/h was implanted sub-cutaneously in the lower-lateral area of the back. The peptides were dissolved in 50% (v/v) propylene glycol in water for filling osmotic minipumps.

After the tumors became visible and palpable, tumor volumes were measured and calculated as described in Szende B., et al. "Growth Inhibition of MXT Mammary Carcinoma by Enhancing Programmed Cell Depth", (apoptosis) with analogues of LH-RH and somatostatin). Breast Cancer Res. Treat. 14: 307-314 (1989).

The experiments were terminated at the exponential phase of tumor growth. The first measurement of tumor volume was at 10 days. The differences in tumor volume between the control and those treated with either bombesin antagonists as well as between both bombesin antagonists are statistically significant. The results of tumor volume measurements appear in Table 2 and are illustrated in FIG. 1.

TABLE 2

Effect of Bombesin Antagonists on Tumor volume of Estrogen independent MXT mouse mammary Cancers

| Peptide | Tumor volume at time (days) | | |
|---|---|---|---|
| | 10 | 14 | 17 |
| Control | 729 | 2565 | 5000 |
| [D—Tpi$^6$—Leu$^{13}$-psi-Leu$^{14}$]—Bn(6–14) ("B1") | 363* | 2437 | 3742* |
| [D—Phe—Leu$^{13}$-psi-Tac$^{14}$]—Bn(6–14), ie Peptide No. 2 | 360* | 1477* | 3323** |
| Surgical Bilateral Ovariectomy | | | |

*p<0.05
**p<0.01

At the termination of the experiments, the mice were exsanguinated under Metofane anesthesia, tumor weights are then measured and subjected to statistical analysis by Duncan's test and Student's test. The results appear in Table 3.

TABLE 3

| Compound Administered to Mice bearing Estrogen Independent MXT Mouse Mammary Tumor | Tumor Weight (g) |
|---|---|
| Control | 8.45 ± 0.23 |
| [D—Tpi$^6$—Leu$^{13}$-psi-Leu$^{14}$] Bn(6-14) | 7.36 ± 0.46 |
| Peptide No. 2 | 5.48 ± 1.00** |

Values are means ± s.e.
**p 0.01

EXAMPLE (8)

The effect of one somatostatin analogue and three bombesin antagonists on human small cell lung carcinoma in nude mice is tested as follows: athymic male nude mice approximately 6 weeks old on arrival, are obtained from the National Cancer Institute (Bethesda, Md.) and are maintained under pathogen limited conditions.

Human small cell lung carcinoma (SCLC, line H69) is grown as a monolayer in rpmi 1640 (Gibco, Grand Island, N.Y.) supplemented with 10% bovine serum albumin, antibiotics and antimycotics at 37° C. in a humidified 5% $CO_2$ atmosphere. Xenografts are initiated by s.c. injection of $1 \times 10^7$ cells from exponentially growing cells of the cell tissue culture into the right flank of five nude mice. The resultant tumors after three weeks are aseptically dissected and mechanically minced. Three $mm^3$ pieces of tumor tissue are then transplanted s.c. by Trocar needle into 60 animals. Two weeks after transplantation, tumors had grown to a volume of approximately 10 $mm^3$ and the animals were randomized and divided into 5 experimental groups for treatment with five different compounds, starting on the day two weeks after transplantation. The tumors were measured each week thereafter for five weeks. Tumor volume is calculated as (length × width × height × pi)/6. Eight animals in each group were sacrificed for measurement of tumor weight.

The first of the drug therapy compounds administered to the nude mice is a somatostatin analogue D-Phe-Cys-Tyr-D-Trp-Lys-Val-Cys-Trp-$NH_2$, herein designated "S1."

The first of the three bombesin antagonists is D-Tpi$^1$-Gln$^2$-Trp$^3$-Ala$^4$-Val$^5$-Gly$^6$-His$^7$-Leu$^8$-$_{psi}$-Leu$^9$-$NH_2$, i.e., B1. The second bombesin antagonist is [Tpi$^6$-Leu$^{13}$-$_{psi}$-Tpi$^{14}$]Bn(6-14), i.e., D-Tpi$^1$-Gln$^2$-Trp$^3$-Ala$^4$-Val$^5$-Gly$^6$-His$^7$-Leu$^8$-$_{psi}$-Tpi$^9$-$NH_2$—designated "B2" and the third antagonist is Peptide 2.

Figure 2:
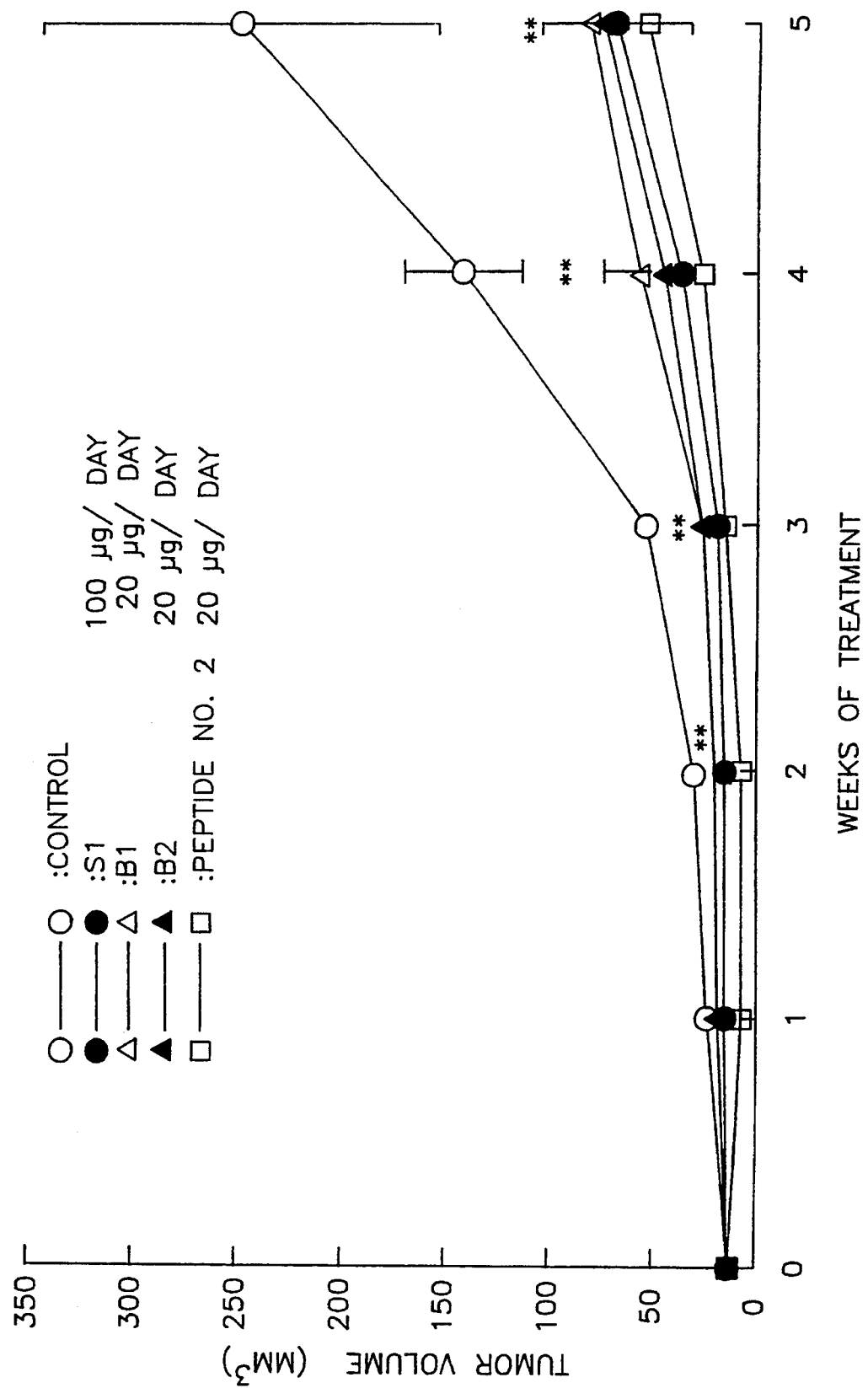
FIG. 2 is a graph depicting the effect on SCLC tumor volume in nude mice of administering certain bombesin antagonists, based on data drawn from Table 4, Example 8.

Microgranules of the pamoate salt of S1 in poly(DL-lactide-coglycolide) are prepared at Cytotech SA and designed to release about 100 microgram/day for 2 weeks from an aliquot of 16 mg. These microgranules are injected every 15 days s.c. at the side opposite to the tumor. Each of the bombesin antagonists is dissolved in 0.1% dimethyl sulfoxide in saline solution and injected s.c. twice daily at a dose of 20 microgram/day. The effect of this drug therapy on tumor volume appears in Table 4 and is illustrated in FIG. 2.

TABLE 4

| Effect of Bombesin Antagonists on Tumor volume of SCLC Tumors | | | | | | |
|---|---|---|---|---|---|---|
| Peptide | | | | Tumor volume at time (days) | | |
|  | 0 | 7 | 14 | 21 | 28 | 35 |
| Control | 10.5 ± 0.5 | 19.3 ± 1.4 | 31.6 ± 5.6 | 63.8 ± 10.6 | 142.8 ± 37.5 | 249.7 ± 74.3 |
| S1 | 9.8 ± 0.8 | 14.4 ± 1.5 | 15.8 ± 1.3 | 18.4 ± 2.9 | 33.2 ± 9.0 | 66.0 ± 12.1 |
| B1 | 11.2 ± 0.8 | 13.3 ± 1.2 | 17 ± 3.4 | 24.7 ± 8.2 | 55 ± 24.5 | 80.2 ± 27.2 |
| B2 | 10 ± 1.1 | 11.7 ± 1.2 | 14.7 ± 2.4 | 24.5 ± 7.9 | 45 ± 15 | 74.1 ± 31.8 |
| Peptide No. 2 | 11.6 ± 1.7 | 7.4 ± 1.8 | 8.9 ± 2.3 | 14.3 ± 6.3 | 19.2 ± 9.4 | 49.0 ± 21.0 |

EXAMPLE (9)

The effect on MIA PACA-2 pancreatic cancer tumors by bombesin antagonists is measured as follows: Nude mice similar to the ones in Example 8 are injected s.c. with MIA PACA-2 human pancreatic cancer cell injection, derived from cell tissue culture grown as is the SCLC, in Example 8. Tumor volume is measured for both experimental groups as in Example 8.

The two experimental groups are: a group of mice receiving bombesin antagonist peptide 2 and a control group receiving only the injection vehicle solution. 50 ug. of the injection vehicle solution or Peptide No. 2 are administered to each mouse twice daily by s.c. injection.

Figure 3:
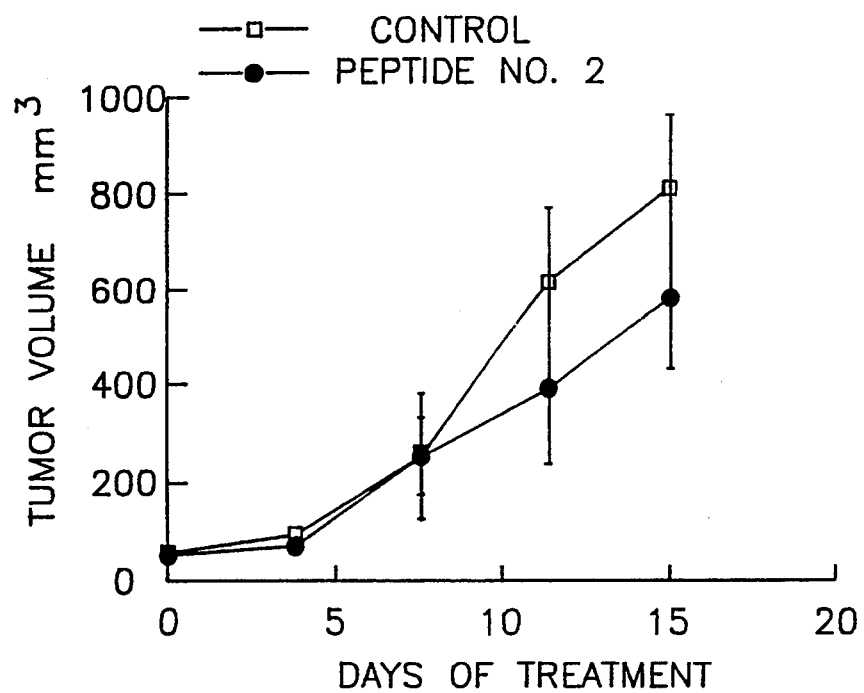
FIG. 3 is a graph depicting the effect on MIA PACA-2 pancreatic tumor volume in nude mice of administering certain bombesin antagonists, based on data drawn from Table 5, Example 9.

The results of tumor volume measurements appear in Table 5 and are illustrated in FIG. 3.

TABLE 5

| Effect of Bombesin Antagonists on Tumor volume ($mm^3$) of MIA PACA-2 pancreatic tumors | | | | |
|---|---|---|---|---|
| Peptide | | Tumor volume at time (days) | | |
|  | 0 | 7 | 11 | 15 |
| Control | 45.6 ± 7.9 | 254.2 ± 59.8 | 645.1 ± 128.6 | 855.9 ± 145.4 |
| Peptide No. 2 | 29.8 ± 4.3 | 252.3 ± 98.9 | 427.9 ± 122.6 | 634.1 ± 174.0 |

EXAMPLE (10)

The effect of treatment with as bombesin antagonist on nude mice bearing CAPAN-2 human pancreatic cancer is as follows.

Nude mice similar to those of Example 7 are given Xenografts of human CAPAN-2 pancreatic tumors derived from cell tissue culture grown as in Example 7. The group of mice is divided into two, with the control group receiving only the injection vehicle solution and the other receiving bombesin antagonist Peptide No. 2, 50mg. of which were administered twice daily by s.c. injection.

Figure 4:
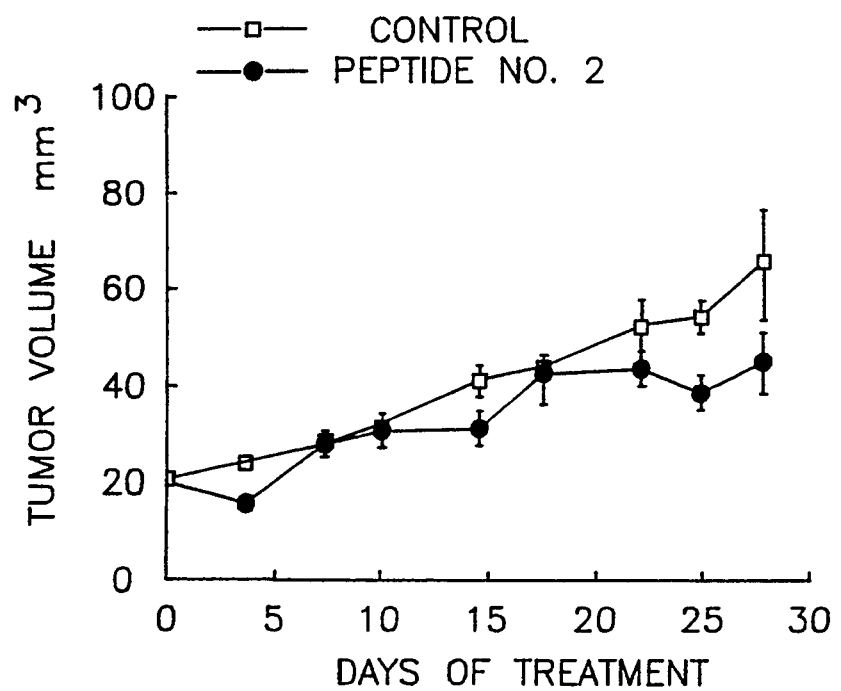
FIG. 4 is a graph depicting the effect on a CAPAN-2 pancreatic tumor volume in nude mice of administering certain bombesin antagonists, based on data drawn from Table 6, Example 10.

Tumor volume is measured as in Example 8 and results of tumor volume measurements appear Table 6 and are illustrated in FIG. 4.

TABLE 6

| | Peptide | | Tumor volume at time (days) | | |
|---|---|---|---|---|---|
| | 0 | 7 | 14 | 21 | 28 |
| Control | 21.2 ± 1.7 | 28.3 ± 2.3 | 43.0 ± 3.6 | 51.4 ± 8.9 | 78.8 ± 16.7 |
| Peptide No. 2 | 19.7 ± 1.7 | 27.8 ± 3.3 | 32.2 ± 3.5 | 46.4 ± 3.0 | 50.5 ± 17.8 |

Table 6: Effect of Bombesin Antagonists on Tumor volume ($mm^3$) of CAPAN pancreatic tumors Although the invention has been described with regard to its preferred embodiments, it should be understood that changes and modifications obvious to one having the ordinary skill in this art may be made without departing from the scope of the invention, which is set forth in the claims which are appended thereto. Substitutions known in the art which do not significantly detract from its effectiveness may be employed in the invention.

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: miscfeature
      ( B ) LOCATION: 1
      ( D ) OTHER INFORMATION: /note="Res 1 =D-pGlu"

( i x ) FEATURE:
      ( A ) NAME/KEY: miscfeature
      ( B ) LOCATION: 8
      ( D ) OTHER INFORMATION: /note=" Res 8 =reduced isostere of Leu"

( i x ) FEATURE:
      ( A ) NAME/KEY: miscfeature
      ( B ) LOCATION: 9
      ( D ) OTHER INFORMATION: /note="Res 9 =Tac-NH2"

( x i ) SEQUENCE DESCRIPTION: SEQ ID NO:1:

Xaa Gln Trp Ala Val Gly His Xaa Xaa
   1                      5

( 2 ) INFORMATION FOR SEQ ID NO:2:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: miscfeature
      ( B ) LOCATION: 1
      ( D ) OTHER INFORMATION: /note="Res 1 =D-Phe"

( i x ) FEATURE:
      ( A ) NAME/KEY: miscfeature
      ( B ) LOCATION: 8
      ( D ) OTHER INFORMATION: /note=" Res 8 =reduced isostere of Leu"

( i x ) FEATURE:
      ( A ) NAME/KEY: miscfeature
      ( B ) LOCATION: 9
      ( D ) OTHER INFORMATION: /note="Res 9 =Tac-NH2"

(x i) SEQUENCE DESCRIPTION: SEQ ID NO:2:

Xaa Gln Trp Ala Val Gly His Xaa Xaa
1               5

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: miscfeature
        (B) LOCATION: 1
        (D) OTHER INFORMATION: /note="Res 1 =D-Phe"

(i x) FEATURE:
        (A) NAME/KEY: miscfeature
        (B) LOCATION: 8
        (D) OTHER INFORMATION: /note=
        " Res 8 =reduced isostere of Leu"

(i x) FEATURE:
        (A) NAME/KEY: miscfeature
        (B) LOCATION: 9
        (D) OTHER INFORMATION: /note="Res 9 =MTac-NH2"

(x i) SEQUENCE DESCRIPTION: SEQ ID NO:3:

Xaa Gln Trp Ala Val Gly His Xaa Xaa
1               5

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: miscfeature
        (B) LOCATION: 1
        (D) OTHER INFORMATION: /note="Res 1 =Ac-D-Phe"

(i x) FEATURE:
        (A) NAME/KEY: miscfeature
        (B) LOCATION: 8
        (D) OTHER INFORMATION: /note=
        " Res 8 =reduced isostere of Leu"

(i x) FEATURE:
        (A) NAME/KEY: miscfeature
        (B) LOCATION: 9
        (D) OTHER INFORMATION: /note="Res 9 =Tac-NH2"

(x i) SEQUENCE DESCRIPTION: SEQ ID NO:4:

Xaa Gln Trp Ala Val Gly His Xaa Xaa
1               5

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: miscfeature (B) LOCATION: 1
(D) OTHER INFORMATION: /note="Res 1 =D-Cpa"

(ix) FEATURE:
    (A) NAME/KEY: miscfeature
    (B) LOCATION: 8
    (D) OTHER INFORMATION: /note=
" Res 8 =reduced isostere of Leu"

(ix) FEATURE:
    (A) NAME/KEY: miscfeature
    (B) LOCATION: 9
    (D) OTHER INFORMATION: /note="Res 9 =Tac-NH2"

(xi) SEQUENCE DESCRIPTION: SEQ ID NO:5:

Xaa Gln Trp Ala Val Gly His Xaa Xaa
1               5

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: miscfeature
        (B) LOCATION: 1
        (D) OTHER INFORMATION: /note="Res 1 =D-Cpa"

(ix) FEATURE:
        (A) NAME/KEY: miscfeature
        (B) LOCATION: 8
        (D) OTHER INFORMATION: /note=
" Res 8 =reduced isostere of Leu"

(ix) FEATURE:
        (A) NAME/KEY: miscfeature
        (B) LOCATION: 9
        (D) OTHER INFORMATION: /note="Res 9 =MTac-NH2"

(xi) SEQUENCE DESCRIPTION: SEQ ID NO:6:

Xaa Gln Trp Ala Val Gly His Xaa Xaa
1               5

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: miscfeature
        (B) LOCATION: 1
        (D) OTHER INFORMATION: /note="Res 1 =D-Nal"

(ix) FEATURE:
        (A) NAME/KEY: miscfeature
        (B) LOCATION: 8
        (D) OTHER INFORMATION: /note=
" Res 8 =reduced isostere of Leu"

(ix) FEATURE:
        (A) NAME/KEY: miscfeature
        (B) LOCATION: 9
        (D) OTHER INFORMATION: /note="Res 9 =Tac-NH2"

(xi) SEQUENCE DESCRIPTION: SEQ ID NO:7:

Xaa Gln Trp Ala Val Gly His Xaa Xaa
1               5

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: miscfeature
        ( B ) LOCATION: 1
        ( D ) OTHER INFORMATION: /note="Res 1 =Pal"

( i x ) FEATURE:
        ( A ) NAME/KEY: miscfeature
        ( B ) LOCATION: 8
        ( D ) OTHER INFORMATION: /note=
        " Res 8 =reduced isostere of Leu"

( i x ) FEATURE:
        ( A ) NAME/KEY: miscfeature
        ( B ) LOCATION: 9
        ( D ) OTHER INFORMATION: /note="Res 9 =Tac-NH2"

( x i ) SEQUENCE DESCRIPTION: SEQ ID NO:8:

Xaa  Gln  Trp  Ala  Val  Gly  His  Xaa  Xaa
1                            5

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: miscfeature
        ( B ) LOCATION: 1
        ( D ) OTHER INFORMATION: /note="Res 1 =D-Pal"

( i x ) FEATURE:
        ( A ) NAME/KEY: miscfeature
        ( B ) LOCATION: 8
        ( D ) OTHER INFORMATION: /note=
        " Res 8 =reduced isostere of Leu"

( i x ) FEATURE:
        ( A ) NAME/KEY: miscfeature
        ( B ) LOCATION: 9
        ( D ) OTHER INFORMATION: /note="Res 9 =Tac-NH2"

( x i ) SEQUENCE DESCRIPTION: SEQ ID NO:9:

Xaa  Gln  Trp  Ala  Val  Gly  His  Xaa  Xaa
1                            5

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: miscfeature
        ( B ) LOCATION: 1
        ( D ) OTHER INFORMATION: /note="Res 1 =D-Trp"

( i x ) FEATURE:

( A ) NAME/KEY: miscfeature
                ( B ) LOCATION: 8
                ( D ) OTHER INFORMATION: /note=
                                        " Res 8 =reduced isostere of Leu"

( i x ) FEATURE:
                ( A ) NAME/KEY: miscfeature
                ( B ) LOCATION: 9
                ( D ) OTHER INFORMATION: /note="Res 9 =Tac-NH2"

( x i ) SEQUENCE DESCRIPTION: SEQ ID NO:10:

Xaa  Gln  Trp  Ala  Val  Gly  His  Xaa  Xaa
    1                        5

( 2 ) INFORMATION FOR SEQ ID NO:11:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: miscfeature
                ( B ) LOCATION: 1
                ( D ) OTHER INFORMATION: /note="Res 1 =Ac-D-Trp"

( i x ) FEATURE:
                ( A ) NAME/KEY: miscfeature
                ( B ) LOCATION: 8
                ( D ) OTHER INFORMATION: /note=
                                        " Res 8 =reduced isostere of Leu"

( i x ) FEATURE:
                ( A ) NAME/KEY: miscfeature
                ( B ) LOCATION: 9
                ( D ) OTHER INFORMATION: /note="Res 9 =Tac-NH2"

( x i ) SEQUENCE DESCRIPTION: SEQ ID NO:11:

Xaa  Gln  Trp  Ala  Val  Gly  His  Xaa  Xaa
    1                        5

( 2 ) INFORMATION FOR SEQ ID NO:12:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: miscfeature
                ( B ) LOCATION: 1
                ( D ) OTHER INFORMATION: /note="Res 1 =Tpi"

( i x ) FEATURE:
                ( A ) NAME/KEY: miscfeature
                ( B ) LOCATION: 8
                ( D ) OTHER INFORMATION: /note=
                                        " Res 8 =reduced isostere of Leu"

( i x ) FEATURE:
                ( A ) NAME/KEY: miscfeature
                ( B ) LOCATION: 9
                ( D ) OTHER INFORMATION: /note="Res 9 =Tac-NH2"

( x i ) SEQUENCE DESCRIPTION: SEQ ID NO:12:

Xaa  Gln  Trp  Ala  Val  Gly  His  Xaa  Xaa
    1                        5

( 2 ) INFORMATION FOR SEQ ID NO:13:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: miscfeature
    ( B ) LOCATION: 1
    ( D ) OTHER INFORMATION: /note="Res 1 =D-Tpi"

( i x ) FEATURE:
    ( A ) NAME/KEY: miscfeature
    ( B ) LOCATION: 8
    ( D ) OTHER INFORMATION: /note=
        " Res 8 =reduced isostere of Leu"

( i x ) FEATURE:
    ( A ) NAME/KEY: miscfeature
    ( B ) LOCATION: 9
    ( D ) OTHER INFORMATION: /note="Res 9 =Tac-NH2"

( x i ) SEQUENCE DESCRIPTION: SEQ ID NO:13:

Xaa Gln Trp Ala Val Gly His Xaa Xaa
1                   5

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: miscfeature
        ( B ) LOCATION: 1
        ( D ) OTHER INFORMATION: /note="Res 1 =Hca-Gln"

( i x ) FEATURE:
        ( A ) NAME/KEY: miscfeature
        ( B ) LOCATION: 7
        ( D ) OTHER INFORMATION: /note="Res 7 =reduced isostere of Leu ( i x ) FEATURE:
        ( A ) NAME/KEY: miscfeature
        ( B ) LOCATION: 8
        ( D ) OTHER INFORMATION: /note="Res 8 =Tac-NH2"

( x i ) SEQUENCE DESCRIPTION: SEQ ID NO:14:

Xaa Trp Ala Val Gly His Xaa Xaa
    1              5

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: miscfeature
        ( B ) LOCATION: 1
        ( D ) OTHER INFORMATION: /note="Res 1 =D-Phe"

( i x ) FEATURE:
        ( A ) NAME/KEY: miscfeature
        ( B ) LOCATION: 8
        ( D ) OTHER INFORMATION: /note=
        " Res 8 =reduced isostere of Leu"

( i x ) FEATURE:
    ( A ) NAME/KEY: miscfeature
    ( B ) LOCATION: 9
    ( D ) OTHER INFORMATION: /note="Res 9 =Tac-NH2"

( x i ) SEQUENCE DESCRIPTION: SEQ ID NO:15:

Xaa His Trp Ala Val Gly His Xaa Xaa
1               5

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: miscfeature
        ( B ) LOCATION: 1
        ( D ) OTHER INFORMATION: /note="Res 1 =D-Phe"

( i x ) FEATURE:
        ( A ) NAME/KEY: miscfeature
        ( B ) LOCATION: 2
        ( D ) OTHER INFORMATION: /note="Res 2 =Glu(OMe)"

( i x ) FEATURE:
        ( A ) NAME/KEY: miscfeature
        ( B ) LOCATION: 8
        ( D ) OTHER INFORMATION: /note=
                      " Res 8 =reduced isostere of Leu"

( i x ) FEATURE:
        ( A ) NAME/KEY: miscfeature
        ( B ) LOCATION: 9
        ( D ) OTHER INFORMATION: /note="Res 9 =Tac-NH2"

( x i ) SEQUENCE DESCRIPTION: SEQ ID NO:16:

Xaa Xaa Trp Ala Val Gly His Xaa Xaa
1               5

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: miscfeature
        ( B ) LOCATION: 1
        ( D ) OTHER INFORMATION: /note="Res 1 =D-Phe"

( i x ) FEATURE:
        ( A ) NAME/KEY: miscfeature
        ( B ) LOCATION: 2
        ( D ) OTHER INFORMATION: /note="Res 2 =Glu[-]"

( i x ) FEATURE:
        ( A ) NAME/KEY: miscfeature
        ( B ) LOCATION: 8
        ( D ) OTHER INFORMATION: /note=
                      " Res 8 =reduced isostere of Leu"

( i x ) FEATURE:
        ( A ) NAME/KEY: miscfeature
        ( B ) LOCATION: 9
        ( D ) OTHER INFORMATION: /note="Res 9 =Tac-NH2"

( x i ) SEQUENCE DESCRIPTION: SEQ ID NO:17:

Xaa Xaa Trp Ala Val Gly His Xaa Xaa (2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: miscfeature
        (B) LOCATION: 1
        (D) OTHER INFORMATION: /note="Res 1 =D-Phe"

(ix) FEATURE:
        (A) NAME/KEY: miscfeature
        (B) LOCATION: 8
        (D) OTHER INFORMATION: /note=
        " Res 8 =reduced isostere of Leu"

(ix) FEATURE:
        (A) NAME/KEY: miscfeature
        (B) LOCATION: 9
        (D) OTHER INFORMATION: /note="Res 9 =DMTac-NH2"

(xi) SEQUENCE DESCRIPTION: SEQ ID NO:18:

Xaa Gln Trp Ala Val Gly His Xaa Xaa
1                   5

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: miscfeature
        (B) LOCATION: 1
        (D) OTHER INFORMATION: /note="Res 1 =Ac-D-Phe"

(ix) FEATURE:
        (A) NAME/KEY: miscfeature
        (B) LOCATION: 8
        (D) OTHER INFORMATION: /note=
        " Res 8 =reduced isostere of Leu"

(ix) FEATURE:
        (A) NAME/KEY: miscfeature
        (B) LOCATION: 9
        (D) OTHER INFORMATION: /note="Res 9 =DMTac-NH2"

(xi) SEQUENCE DESCRIPTION: SEQ ID NO:19:

Xaa Gln Trp Ala Val Gly His Xaa Xaa
1                   5

(2) INFORMATION FOR SEQ ID NO:20:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: miscfeature
        (B) LOCATION: 1
        (D) OTHER INFORMATION: /note="Res 1 =D-Cpa"

( i x ) FEATURE:
        ( A ) NAME/KEY: miscfeature
        ( B ) LOCATION: 8
        ( D ) OTHER INFORMATION: /note=
                                        " Res 8 =reduced isostere Leu"

( i x ) FEATURE:
        ( A ) NAME/KEY: miscfeature
        ( B ) LOCATION: 9
        ( D ) OTHER INFORMATION: /note="Res 9 =DMTac-NH2"

( x i ) SEQUENCE DESCRIPTION: SEQ ID NO:20:

Xaa Gln Trp Ala Val Gly His Xaa Xaa
1               5

( 2 ) INFORMATION FOR SEQ ID NO:21:

( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: miscfeature
            ( B ) LOCATION: 1
            ( D ) OTHER INFORMATION: /note="Res 1 =Tpi"

( i x ) FEATURE:
            ( A ) NAME/KEY: miscfeature
            ( B ) LOCATION: 8
            ( D ) OTHER INFORMATION: /note=
                                            " Res 8 =reduced isostere of Leu"

( i x ) FEATURE:
            ( A ) NAME/KEY: miscfeature
            ( B ) LOCATION: 9
            ( D ) OTHER INFORMATION: /note="Res 9 =DMTac-NH2"

( x i ) SEQUENCE DESCRIPTION: SEQ ID NO:21:

Xaa Gln Trp Ala Val Gly His Xaa Xaa
1               5

( 2 ) INFORMATION FOR SEQ ID NO:22:

( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: miscfeature
            ( B ) LOCATION: 1
            ( D ) OTHER INFORMATION: /note="Res 1 =D-Tpi"

( i x ) FEATURE:
            ( A ) NAME/KEY: miscfeature
            ( B ) LOCATION: 8
            ( D ) OTHER INFORMATION: /note=
                                            " Res 8 =reduced isostere of Leu"

( i x ) FEATURE:
            ( A ) NAME/KEY: miscfeature
            ( B ) LOCATION: 9
            ( D ) OTHER INFORMATION: /note="Res 9 =DMTac-NH2"

( x i ) SEQUENCE DESCRIPTION: SEQ ID NO:22:

Xaa Gln Trp Ala Val Gly His Xaa Xaa
1               5

( 2 ) INFORMATION FOR SEQ ID NO:23:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: miscfeature
    (B) LOCATION: 1
    (D) OTHER INFORMATION: /note="Res 1 =pGlu"

(ix) FEATURE:
    (A) NAME/KEY: miscfeature
    (B) LOCATION: 14
    (D) OTHER INFORMATION: /note="Res 14 =Met-NH2"

(xi) SEQUENCE DESCRIPTION: SEQ ID NO:23:

Xaa Gln Arg Leu Gly Asn Gln Trp Ala Val Gly His Leu Xaa
1               5                   10

(2) INFORMATION FOR SEQ ID NO:24:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: miscfeature
    (B) LOCATION: 1
    (D) OTHER INFORMATION: /note="Res 1 =H-Gly"

(ix) FEATURE:
    (A) NAME/KEY: miscfeature
    (B) LOCATION: 10
    (D) OTHER INFORMATION: /note="Res 10 =Met-NH2"

(xi) SEQUENCE DESCRIPTION: SEQ ID NO:24:

Xaa Asn His Trp Ala Val Gly His Leu Xaa
1               5                   10

(2) INFORMATION FOR SEQ ID NO:25:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: miscfeature
    (B) LOCATION: 9
    (D) OTHER INFORMATION: /note="Res 9 =Met-NH2"

(xi) SEQUENCE DESCRIPTION: SEQ ID NO:25:

Asn His Trp Ala Val Gly His Leu Xaa
1               5

(2) INFORMATION FOR SEQ ID NO:26:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (ix) FEATURE:
  (A) NAME/KEY: miscfeature
  (B) LOCATION: 11
  (D) OTHER INFORMATION: /note="Res 11 =Met-NH2"

(xi) SEQUENCE DESCRIPTION: SEQ ID NO:26:

Arg Pro Lys Pro Gln Gln Phe Phe Gly Leu Xaa
1               5                   10

(2) INFORMATION FOR SEQ ID NO:27:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: miscfeature
    (B) LOCATION: 1
    (D) OTHER INFORMATION: /note=
        " Res 1 =(R1)(R2)-A0-A1, where A0
        = deleted; A1 =D-Phe, D-Trp or
        D-Nal; R1 and R2 =H"

(ix) FEATURE:
    (A) NAME/KEY: miscfeature
    (B) LOCATION: 8
    (D) OTHER INFORMATION: /note=
        " Res 8 =A8-W, where W =-N(R8)-
        CH(Z1)-R4- CH(Z2)-CO-V, where
        R4 =CH2NH; Z1 =-CH2CH(CH3)2;
        Z2 =- CH2SH or (CH2)2-S-CH3;
        V =N(R6)R7, where R6, R7 and R8 may
        be H; R1 and R2 may =H or COE1, where
        E1 =C1- 20 alkyl"

(xi) SEQUENCE DESCRIPTION: SEQ ID NO:27:

Xaa Gln Trp Ala Val Gly His Xaa
1               5

(2) INFORMATION FOR SEQ ID NO:28:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: miscfeature
    (B) LOCATION: 1
    (D) OTHER INFORMATION: /note=
" Res 1 =X-A1, where X =H, a
single bond linking alpha amino group of A1 to gamma carboxyl on 3-
propionyl of Glu when Res 2 =Glu; or R1CO, where R1 =H, C1-10-alkyl,
phenyl, phenyl-C1-10-alkyl, p-Hl-phenyl, p-hl-phenyl-C1-10- alkyl,
naphthyl, naphthyl-C1-10-alkyl, indolyl, indolyl-C1-10- alkyl, pyridyl,
pyridyl-C1-10-alkyl; thienyl, thienyl-C1-10-alkyl, cyclohexyl or
cyclohexyl-C1-10-alkyl, where Hl =F, Cl, Br, OH, CH3, or OCH3; or R1 =
N(R2)(R3), where R2 =H, C1-10-alkyl, phenyl or phenyl-C1- 10-alkyl; R3 =
H or C1-10 alkyl; or R1 =R4O, where R4 =C1-10 alkyl, phenyl or
phenyl-C1-10-alkyl; and A1 =D-, L- or DL-amino acid residue selected
from Phe, p-Hl-Phe, pGlu, Nal, Pal, Tpi, unsubstituted Trp or Trp
substituted in the benzene ring by one or of F, Cl, Br, NH2 or C1-3
alkyl; or a peptide bond linking the acyl moiety of R1CO to the alpha
amino moiety of Res 2"

(ix) FEATURE:
    (A) NAME/KEY: miscfeature
    (B) LOCATION: 2
    (D) OTHER INFORMATION: /note=
        " Res 2 =Gln, Glu[-], Glu (Y) or His"

( i x ) FEATURE:
        ( A ) NAME/KEY: miscfeature
        ( B ) LOCATION: 8
        ( D ) OTHER INFORMATION: /note=
                                    " Res 8 =reduced isostere of Leu"

( i x ) FEATURE:
        ( A ) NAME/KEY: miscfeature
        ( B ) LOCATION: 9
        ( D ) OTHER INFORMATION: /note="Res 9 =A9-Q, where A9 =Tac,
              MTac or DMTac; and Q =NH2 or OQ1, where Q1 =H, phenyl
              or phenyl-C1- 10-alkyl"

( x i ) SEQUENCE DESCRIPTION: SEQ ID NO:28:

Xaa Xaa Trp Ala Val Gly His Xaa Xaa
 1               5

( 2 ) INFORMATION FOR SEQ ID NO:29:

( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: miscfeature
            ( B ) LOCATION: 1
            ( D ) OTHER INFORMATION: /note="Res 1 =D-Phe"

( i x ) FEATURE:
            ( A ) NAME/KEY: miscfeature
            ( B ) LOCATION: 8
            ( D ) OTHER INFORMATION: /note=
                                        " Res 8 =reduced isostere of Leu"

( i x ) FEATURE:
            ( A ) NAME/KEY: miscfeature
            ( B ) LOCATION: 9
            ( D ) OTHER INFORMATION: /note="Res 9 =Tac-NH2"

( x i ) SEQUENCE DESCRIPTION: SEQ ID NO:29:

Xaa Glu Trp Ala Val Gly His Xaa Xaa
 1               5

( 2 ) INFORMATION FOR SEQ ID NO:30:

( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: miscfeature
            ( B ) LOCATION: 1
            ( D ) OTHER INFORMATION: /note="Res 1 =D-Tpi"

( i x ) FEATURE:
            ( A ) NAME/KEY: miscfeature
            ( B ) LOCATION: 8
            ( D ) OTHER INFORMATION: /note=
                                        " Res 8 =reduced isostere of Leu"

( i x ) FEATURE:
            ( A ) NAME/KEY: miscfeature
            ( B ) LOCATION: 9
            ( D ) OTHER INFORMATION: /note="Res 9 =Leu-NH2"

( x i ) SEQUENCE DESCRIPTION: SEQ ID NO:30:

Xaa Gln Trp Ala Val Gly His Xaa Xaa
 1               5

( 2 ) INFORMATION FOR SEQ ID NO:31:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: miscfeature
        ( B ) LOCATION: 1
        ( D ) OTHER INFORMATION: /note="Res 1 =D-Phe"

( i x ) FEATURE:
        ( A ) NAME/KEY: miscfeature
        ( B ) LOCATION: 4
        ( D ) OTHER INFORMATION: /note="Res 4 =D-Trp"

( i x ) FEATURE:
        ( A ) NAME/KEY: miscfeature
        ( B ) LOCATION: 8
        ( D ) OTHER INFORMATION: /note="Res 8 =Trp-NH2"

( x i ) SEQUENCE DESCRIPTION: SEQ ID NO:31:

```
Xaa  Cys  Tyr  Xaa  Lys  Val  Cys  Xaa
 1                    5
```

( 2 ) INFORMATION FOR SEQ ID NO:32:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: miscfeature
        ( B ) LOCATION: 1
        ( D ) OTHER INFORMATION: /note="Res 1 =D-Tpi"

( i x ) FEATURE:
        ( A ) NAME/KEY: miscfeature
        ( B ) LOCATION: 8
        ( D ) OTHER INFORMATION: /note=
                " Res 8 =reduced isostere of Leu"

( i x ) FEATURE:
        ( A ) NAME/KEY: miscfeature
        ( B ) LOCATION: 9
        ( D ) OTHER INFORMATION: /note="Res 9 =Tpi-NH2"

( x i ) SEQUENCE DESCRIPTION: SEQ ID NO:32:

```
Xaa  Gln  Trp  Ala  Val  Gly  His  Xaa  Xaa
 1                    5
```

( 2 ) INFORMATION FOR SEQ ID NO:33:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: miscfeature
        ( B ) LOCATION: 1
        ( D ) OTHER INFORMATION: /note=
                " Res 1 =X-A1, where X =H or Ac;
                A1 =D- Phe, L- or D-Tpi"

( i x ) FEATURE:

-continued (A) NAME/KEY: miscfeature
              (B) LOCATION: 8
              (D) OTHER INFORMATION: /note=
                                              "Res 8 = reduced isostere of Leu"

(ix) FEATURE:
              (A) NAME/KEY: miscfeature
              (B) LOCATION: 9
              (D) OTHER INFORMATION: /note="Res 9 = Tac-NH2"

(xi) SEQUENCE DESCRIPTION: SEQ ID NO:33:

Xaa  Gln  Trp  Ala  Val  Gly  His  Xaa  Xaa
     1                   5

(2) INFORMATION FOR SEQ ID NO:34:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: miscfeature
              (B) LOCATION: 1
              (D) OTHER INFORMATION: /note=
                                              "Res 1 = X-A1, where X = H or Ac;
                                              A1 = D- Phe, L- or D-Tpi"

(ix) FEATURE:
              (A) NAME/KEY: miscfeature
              (B) LOCATION: 8
              (D) OTHER INFORMATION: /note=
                                              "Res 8 = reduced isostere of Leu"

(ix) FEATURE:
              (A) NAME/KEY: miscfeature
              (B) LOCATION: 9
              (D) OTHER INFORMATION: /note="Res 9 = DMTac-NH2"

(xi) SEQUENCE DESCRIPTION: SEQ ID NO:34:

Xaa  Gln  Trp  Ala  Val  Gly  His  Xaa  Xaa
     1                   5

(2) INFORMATION FOR SEQ ID NO:35:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: miscfeature
              (B) LOCATION: 1
              (D) OTHER INFORMATION: /note=
"Res 1 = X-A1, where X = H, a
single bond linking alpha amino group of A1 to gamma carboxyl on 3-pro-
pionyl of Glu when Res 2 = Glu; or R1CO, where R1 = H, C1-10-alkyl,
phenyl, phenyl-C1-10-alkyl; or R1 = N(R2)(R3), where R2 = H, C1-10
alkyl, phenyl or phenyl-C1-10-alkyl; R3 = H or C1-10 alkyl; or
R1 = R4O, where R4 = C1-10 alkyl, phenyl or phenyl-C1- 10-alkyl; and
A1 = L- or D-Pal or L-or D-Tpi;

(ix) FEATURE:
              (A) NAME/KEY: miscfeature
              (B) LOCATION: 2
              (D) OTHER INFORMATION: /note=
                                              "Res 2 = Gln, Glu [-], Glu (Y) or His"

(ix) FEATURE:
              (A) NAME/KEY: miscfeature
              (B) LOCATION: 8
              (D) OTHER INFORMATION: /note=

"Res 8 =reduced isostere of Leu"

(ix) FEATURE:
    (A) NAME/KEY: miscfeature
    (B) LOCATION: 9
    (D) OTHER INFORMATION: /note=

"Res 9 =A9-Q, where A9 =Cys or Pen; and Q =NH2 or OQ1 where Q1 =H, C1- 10-alkyl, phenyl or phenyl-C1-10-alkyl"

(xi) SEQUENCE DESCRIPTION: SEQ ID NO:35:

Xaa Xaa Trp Ala Val Gly His Xaa Xaa
1                 5

(2) INFORMATION FOR SEQ ID NO:36:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: miscfeature
        (B) LOCATION: 1
        (D) OTHER INFORMATION: /note=

"Res 1 =X-A1-Gln, where X =Hca, Hna, Paa, Mpp, Hpp or Naa; and A1 =a peptide bond linking the acyl moiety of X to the alpha amino moiety of Gln"

(ix) FEATURE:
        (A) NAME/KEY: miscfeature
        (B) LOCATION: 7
        (D) OTHER INFORMATION: /note=

"Res 7 =reduced isostere of Leu"

(ix) FEATURE:
        (A) NAME/KEY: miscfeature
        (B) LOCATION: 8
        (D) OTHER INFORMATION: /note="Res 8 =Tac-NH2"

(xi) SEQUENCE DESCRIPTION: SEQ ID NO:36:

Xaa Trp Ala Val Gly His Xaa Xaa
1             5

(2) INFORMATION FOR SEQ ID NO:37:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: miscfeature
        (B) LOCATION: 1
        (D) OTHER INFORMATION: /note="Res 1 =pGlu"

(ix) FEATURE:
        (A) NAME/KEY: miscfeature
        (B) LOCATION: 9
        (D) OTHER INFORMATION: /note="Res 9 =Met-NH2"

(xi) SEQUENCE DESCRIPTION: SEQ ID NO:37:

Xaa Gln Trp Ala Val Gly His Leu Xaa
1                 5

We claim:

1. A bombesin antagonist peptide having the formula:

$$X\text{-}A^1\text{-}A^2\text{-}Trp\text{-}Ala\text{-}Val\text{-}Gly\text{-}His\text{-}Leu\text{-}\psi\text{-}A^9\text{-}Q$$

wherein
X is hydrogen,
a single bond linking the alpha amino group of $A^1$ to the gamma carboxyl moiety on the 3-propionyl moiety of $A^2$ when $A^2$ is Glu[—], or
a group of formula $R^1CO$—, wherein $R^1$ is selected from the groups consisting of
  a) hydrogen, $C_{1-10}$ alkyl, phenyl, phenyl-$C_{1-10}$-alkyl, p-HI-phenyl, p-HI-phenyl-$C_{1-10}$-alkyl, naphthyl, naphthyl-$C_{1-10}$-alkyl, indolyl, indolyl-$C_{1-10}$-alkyl, pyridyl, pyridyl-$C_{1-10}$-alkyl, thienyl, thienyl-$C_{1-10}$-alkyl, cyclohexyl or cyclohexyl-$C_{1-10}$-alkyl, where HI =F, Cl, Br, OH, $CH_3$ or $OCH_3$;
  b)

wherein
$R^2$ is hydrogen, $C_{1-10}$ alkyl, phenyl or phenyl-$C_{1-10}$-alkyl,
$R^3$ is hydrogen or $C_{1-10}$ alkyl;
  c) $R^4$—O wherein $R^4$ is $C_{1-10}$ alkyl, phenyl or phenyl-$C_{1-10}$-alkyl;
$A^1$ is a D- or L-amino acid residue selected from the group consisting of Phe, p-HI-Phe, pGlu, Nal, Pal, Tpi, unsubstituted Trp or Trp substituted in the benzene ring by one or more members selected from the group consisting of F, Cl, Br, $NH_2$ or $C_{1-3}$ alkyl;
or a peptide bond linking the acyl moiety of $R^1$—CO to the alpha amino moiety of $A^2$, provided $X=R^1CO$;
$A^2$ is Gln, Glu[—], Glu(Y), or His, wherein
[—] is a single bond when X is a single bond and $A^2$ is Glu[—], said[—] linking the gamma carboxyl moiety on the 3-propionyl moiety of said $A^2$ with the alpha amino group of $A^1$,
Y is
  a) —$OR^5$ wherein $R^3$ is hydrogen, $C_{1-10}$ alkyl or phenyl; or
  b),

wherein
$R^6$ is hydrogen or $C_{1-3}$ alkyl; and
$R^7$ is hydrogen, $C_{1-3}$ alkyl or—$NHCONH_2$;
Leu-$psi$- is a reduced form of Leu wherein the C=O moiety is instead —$CH_2$— such that the bond of this —$CH_2$— moiety with the alpha amino group of the adjacent $A^9$ residue is a pseudopeptide bond;
$A^9$ is Tac, MTac or DMTac; and
Q is $NH_2$ or $OQ^1$ where $Q^1$ is hydrogen, $C_{1-10}$ alkyl, phenyl or phenyl-$C_{1-10}$-alkyl;
and the pharmaceutically acceptable acids or salts thereof.

2. A peptide according to claim 1 wherein
X is hydrogen, or $R^1CO$ wherein R is H or $C_{1-10}$-alkyl;
$A^1$ is D-Cpa, D-Nal, L- or D-Pal, D-Phe, L- or D-Tpi, or D-Trp;

$A^2$ is Gln or His; and
Q is $NH_2$.

3. A peptide according to claim 2 wherein
$A^9$ is Tac.

4. A peptide according to claim 2 wherein
$A^9$ is DMTac.

5. A peptide according to claim 3 wherein
X is H or Ac,
$A^1$ is D-Phe, L- or D-Tpi, and
$A^2$ is Gln.

6. A peptide according to claim 4 wherein
X is H or Ac,
$A^1$ is D-Phe, L- or D-Tpi, and
$A^2$ is Gln.

7. A peptide according to claim 3 of the formula

Seq ID No. 2

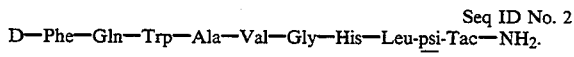
D—Phe—Gln—Trp—Ala—Val—Gly—His—Leu-psi-Tac—$NH_2$.

8. A peptide according to claim 3 of the formula:

Seq ID No. 13

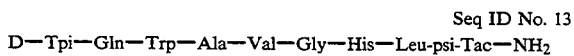
D—Tpi—Gln—Trp—Ala—Val—Gly—His—Leu-psi-Tac—$NH_2$

9. A peptide according to claim 4 of the formula

Seq ID No. 18

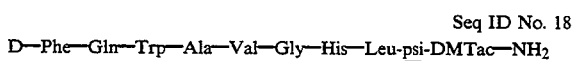
D—Phe—Gln—Trp—Ala—Val—Gly—His—Leu-psi-DMTac—$NH_2$

10. A bombesin antagonist peptide having the formula:

$X-A^1-A^2$-Trp-Ala-Val-Gly-His-Leu-$psi$-$A^9$-Q wherein
X is hydrogen,
a single bond linking the alpha amino group of $A^1$ to the gamma carboxyl moiety on the 3-propionyl moiety of $A^2$ when $A^2$ is Glu[—]; or
a group of formula $R^1CO$—, wherein $R^1$ is selected from the groups consisting of:
  a) hydrogen, $C_{1-10}$ alkyl, phenyl or phenyl-$C_{1-10}$-alkyl;
  b)

wherein
$R^2$ is hydrogen, $C_{1-10}$ alkyl, phenyl or phenyl-$C_{1-10}$-alkyl,
$R^3$ is hydrogen or $C_{1-10}$ alkyl;
  c) $R^4$—O wherein $R^4$ is $C_{1-10}$ alkyl, phenyl or phenyl-$C_{1-10}$-alkyl;
$A^1$ is a non-naturally occurring amino acid selected from the group consisting of L- or D-Pal, or L- or D-Tpi;
$A^2$ is Gln, Glu [—], Glu (Y), or His, wherein
[—] is a single bond when X is a single bond and $A^2$ is Glu[—], said [—] linking the gamma carboxyl moiety on the 3-propionyl moiety of said $A^2$ with the alpha amino group of $A^1$,
Y is a) —OR⁵ wherein R⁵ is hydrogen, $C_{1-3}$ alkyl or phenyl; or b)

wherein R⁶ is hydrogen or $C_{1-3}$ alkyl; and R⁷ is hydrogen, $C_{1-3}$ alkyl or —NHCONH₂;

Leu-$_{psi}$- is a reduced form of Leu wherein the C=O moiety is instead —CH₂— such that the bond of this —CH²— moiety with the alpha amino group of the adjacent A⁹ residue is a pseudopeptide bond, A⁹ is Cys or Pen; and Q is NH₂ or OQ¹ where Q¹ is hydrogen, $C_{1-10}$ alkyl, phenyl or phenyl-$C_{1-10}$-alkyl;

and the pharmaceutically acceptable acids or salts thereof.

11. A bombesin antagonist peptide according to claim 1 wherein

X is R¹CO—,

A¹ is a peptide bond linking the acyl moiety of R₁CO— to the alpha amino moiety of A²;

A² is Gln or His; and

Q is NH₂.

12. A peptide according to claim 11 wherein

X is Hca, Hna, Paa, Mpp, Hpp, or Naa,

A² is Gln, and

A⁹ is Tac.

13. A peptide according to claim 12 of the formula

Seq ID. No. 14
Hca—Gln—Trp—Ala—Val—Gly—His—Leu-psi-Tac—NH₂.

14. A pharmaceutical composition which comprises a polypeptide of claim 1, a therapeutically acceptable addition salt form, or a complex thereof and a pharmaceutically acceptable liquid or solid carrier thereof.

15. A method of treating pancreatic cancer in a mammal which comprises administering to said mammal an effective dose of a polypeptide of claim 1, or a therapeutically acceptable acid or salt thereof.

16. A peptide according to claim 1 wherein A² is Gln, A⁹ is Tac and Q is NH₂.

17. A peptide according to claim 16 wherein A¹ is a D- or L- residue selected from the group consisting of Phe, p-HI-Phe and Trp.

18. A peptide selected from the group consisting of:

D—Phe—Gln—Trp—Ala—Val—Gly—His—Leu-psi-Tac—NH₂,

D—Phe—Gln—Trp—Ala—Val—Gly—His—Leu-psi-MTac—NH₂,

Ac—D—Phe—Gln—Trp—Ala—Val—Gly—His—Leu-psi-Tac—NH₂,

D—Trp—Gln—Trp—Ala—Val—Gly—His—Leu-psi-Tac—NH₂,

Ac—D—Trp—Gln—Trp—Ala—Val—Gly—His—Leu-psi-Tac—NH₂,

D—Tpi—Gln—Trp—Ala—Val—Gly—His—Leu-psi-Tac—NH₂,

D—Phe—His—Trp—Ala—Val—Gly—His—Leu-psi-Tac—NH₂, and

D—Phe—Gln—Trp—Ala—Val—Gly—His—Leu-psi-DMTac—NH₂.

19. A peptide according to claim 18 having the formula of:

D-Tpi-Gln-Trp-Ala-Val-Gly-His-Leu-$_{psi}$-Tac-NH₂.

20. A peptide according to claim 18 having the formula of:

D-Phe-Gln-Trp-Ala-Val-Gly-His-Leu-$_{psi}$-DMTac-NH₂.

* * * * *